(12) United States Patent
Rodriguez Sarmiento et al.

(10) Patent No.: US 8,921,397 B2
(45) Date of Patent: *Dec. 30, 2014

(54) BENZOFURANE-PIPERIDINE COMPOUNDS

(75) Inventors: Rosa Maria Rodriguez Sarmiento, Basel (CH); Juergen Wichmann, Steinen (DE)

(73) Assignee: Hoffmann-La Roche Inc., Nutley, NJ (US)

(*) Notice: Subject to any disclaimer, the term of this patent is extended or adjusted under 35 U.S.C. 154(b) by 64 days.

This patent is subject to a terminal disclaimer.

(21) Appl. No.: 13/457,532

(22) Filed: Apr. 27, 2012

(65) Prior Publication Data

US 2012/0283254 A1   Nov. 8, 2012

(30) Foreign Application Priority Data

May 4, 2011 (EP) .................................... 11164716

(51) Int. Cl.
| | | |
|---|---|---|
| A61K 31/4525 | (2006.01) | |
| C07D 405/10 | (2006.01) | |
| C07D 405/14 | (2006.01) | |
| A61K 31/343 | (2006.01) | |
| C07D 417/14 | (2006.01) | |
| C07D 405/04 | (2006.01) | |
| C07D 413/14 | (2006.01) | |

(52) U.S. Cl.
CPC ............ *A61K 31/343* (2013.01); *C07D 405/14* (2013.01); *A61K 31/4525* (2013.01); *C07D 417/14* (2013.01); *C07D 405/04* (2013.01); *C07D 405/10* (2013.01); *C07D 413/14* (2013.01)
USPC .......................................... 514/320; 546/196

(58) Field of Classification Search
USPC .......................................... 514/320; 546/196
See application file for complete search history.

(56) References Cited

U.S. PATENT DOCUMENTS

| 6,090,812 | A | 7/2000 | Feenstra et al. |
| 6,140,345 | A | 10/2000 | Strupczewski et al. |
| 6,335,326 | B1 | 1/2002 | Den Hartog et al. |
| 7,772,252 | B2* | 8/2010 | Hendrix et al. ............... 514/316 |
| 7,795,437 | B2 | 9/2010 | Gobbi et al. |
| 7,825,123 | B2 | 11/2010 | Gobbi et al. |
| 7,858,630 | B2 | 12/2010 | Gobbi et al. |
| 7,939,535 | B2 | 5/2011 | Gobbi et al. |
| 2003/0229066 | A1 | 12/2003 | Hendrix et al. |
| 2010/0075981 | A1 | 3/2010 | Gobbi et al. |
| 2010/0075983 | A1 | 3/2010 | Gobbi et al. |
| 2010/0075985 | A1 | 3/2010 | Prior et al. |
| 2011/0313151 | A1 | 12/2011 | Gobbi et al. |

FOREIGN PATENT DOCUMENTS

| EP | 1688412 | 8/2006 |
| EP | 1870405 | 12/2007 |
| ES | 2131020 | 7/1999 |
| WO | 94/27992 | 12/1994 |
| WO | 95/11680 | 5/1995 |
| WO | 98/34933 | 8/1998 |
| WO | 02/066446 | 8/2002 |
| WO | 2004/026864 | 4/2004 |
| WO | 2004/100954 | 11/2004 |
| WO | 2004/100955 | 11/2004 |
| WO | 2006/082456 | 8/2006 |
| WO | 2007/093540 | 8/2007 |
| WO | 2007/148208 | 12/2007 |
| WO | 2009/013212 | 1/2009 |
| WO | WO2009/013212 | * 1/2009 |
| WO | 2009/019174 | 2/2009 |
| WO | 2010/031735 | 3/2010 |
| WO | 2010/034646 | 4/2010 |
| WO | 2010/034648 | 4/2010 |
| WO | 2011/161009 | 12/2011 |
| WO | 2012/004206 | 1/2012 |

OTHER PUBLICATIONS

Thornber "Isosterism and molecular modi . . . " Chem. Soc. Rev. v. 8, p. 563-580 (1979).*
Pompeiano et al., Brain Res. Mol. 23:163-178 ( 1994).
Ashby et al., "Synapse" 48:154-156 ( 2003).
Gurevich, E.V. et al., Arch. Gen. Psychiatry 54:225-232 ( 1997).
Roth et al., Pharmacol. Ther. 79:231-257 ( 1998).
De Angelis, L., Curr. Opin. Investig. Drugs. 3:106-112 ( 2002).
Howard et al., "Annual Reports in Medicinal Chemistry" 28:39 ( 1993).
Vorel et al., "The Journal of Neuroscience" 22:9595-9603 ( 2002).
Moore et al., "European Journal of Pharmacology" 237:1-7 ( 1993).
Levitan et al., "Journal of Affective Disorders" 71:229-233 ( 2002).
Gurevich, E.V. et al., Neuropsychopharmacology 20:60-80 ( 1999).
Campos et al., "Society for Neuroscience Abstract" 322:8.
Gackenheimer et al., "Journal of Pharmacology & Experimental Therapeutics" 274:1558-1565 ( 1995).
(International Search Report for PCT/EP2009/061788 Nov. 10, 2009).
Patani et al., Chem. Rev. 96:3147-3176 ( 1996).
Drescher et al., "Am. Soc. Neurosci." 894:6 ( 2002).
(Chilean Office Action for CL2162-08 May 26, 2011).
Porras et al., Neuropsychopharmacology 26:311-324 ( 2002).
Leikin et al., Med. Toxicol. Adverse Drug Exp. 4:324-350 ( 1989).
Harrison, P.J., Br. J. Psychiatry Suppl. 38:12-22 ( 1999).
Wustrow, Journal of Medicinal Chemistry 41:760-771 ( 1998).
Pazos et al., Neuroscience:123-139 ( 1987).

(Continued)

*Primary Examiner* — Celia Chang

(57) ABSTRACT

The present invention is concerned with novel selective dual modulators of the 5-$HT_{2A}$ and $D_3$ receptors of formula (I)

(I)

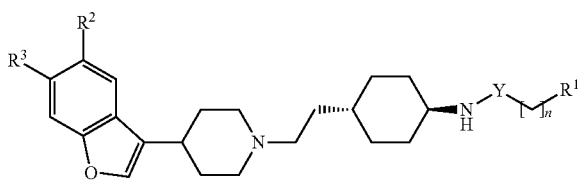

wherein $R^1$, $R^2$, $R^3$, n, and Y are as described herein, as well as pharmaceutically acceptable salts and esters thereof. Further the present invention is concerned with the manufacture of the compounds of formula (I), pharmaceutical compositions comprising them and their use as pharmaceuticals.

24 Claims, No Drawings

(56) References Cited

OTHER PUBLICATIONS

Retz et al., "Journal of Neural. Transmission" 110:531-572 (2003).
Spurlock et al., Mol. Psychiatry 3:42-49 (1998).
Roth et al., Nat. Rev. Drug Discovery 3:353-359 (2004).
Arranz et al., Lancet 355:1615-1616 (2000).
Wiecki et al., "Psychopharmacology" 204:265-277 (2009).
Barnes, N.M., Neuropsychopharmacology 38:1083-1152 (1999).
PCT International Search Report—PCT/EP2011/060080—Mailing date Aug. 1, 2011.
Belliotti, T. R., "Bioorganic & Medicinal Chemistry Lett." 7:2403 (1997).
Ravina et al., J. Med. Chem 42:2774-2797 (1999).
(International Search Report for PCT/EP2008/059356 Apr. 15, 2009).
Lieberman et al., New Eng. J. Med. 353:1209-1223 (2005).
Missale et al., Physiol. Rev. 78:189-225 (1998).
PCT International Search Report—PCT/EP2011/061167—Mailed Sep. 22, 2011.
Gobbi et al., "CA 147:300997 (2007)".
Mach et al., "ChemBioChem." 5(4):508-518 (2004).
(Hansen Chem Abstract 122:2140571995).
Joyce, J.N. et al., Drug Discovery Today 1 10(13):917-925 (2005).
Millan et al., "The Journal of Pharmacology & Experimental Therapeutics" 324:1212-1226 (2008).
(International Search Report for PCT/EP2011/072403 Feb. 2, 2012).
Reavill et al., "The Journal of Pharmacology & Experimental Therapeutics" 294:1154-1165 (2000).
(Intenraitonal Search Report in Corres App PCT/EP2012/057965 Jun. 22, 2012).

\* cited by examiner

US 8,921,397 B2

BENZOFURANE-PIPERIDINE COMPOUNDS

PRIORITY TO RELATED APPLICATION(S)

This application claims the benefit of European Patent Application No. 11164716.0, filed May 4, 2011, which is hereby incorporated by reference in its entirety.

BACKGROUND OF THE INVENTION

Psychotic disorders encompass a variety of diseases, which include schizophrenia, positive, negative and/or cognitive symptoms associated with schizophrenia, schizoaffective disorders, bipolar disease, mania, psychotic depression, and other psychoses involving paranoia and delusions.

In particular schizophrenia is characterized by complex symptomatology including positive symptoms, (i.e. delusions and hallucinations), and negative symptoms, (i.e. anhedonia, restricted fluency and productivity of thought and speech). In addition it is now well recognized that cognitive impairment is the third major diagnostic category of schizophrenia, characterized by loss in working memory as well as other deficits. Other symptoms include aggressiveness, depression and anxiety (Stahl, S. M., *Essential Psychopharmacology. Neuroscientific Basis and Practical Applications* (2000) $2^{nd}$ edition, Cambridge University Press, Cambridge, UK).

Dopamine, a major catecholamine neurotransmitter, is involved in the regulation of a variety of functions, which include emotion, cognition, motor functions, and positive reinforcement. The biological activities of dopamine are mediated through G protein-coupled receptors (GPCRs) and in human, five different dopamine receptors $D_1$-$D_5$ have been identified, where the $D_2$-like receptors ($D_2$, $D_3$ and $D_4$) couple to the G-protein $G_{\alpha i}$. The $D_3$ dopamine receptor is most highly expressed in the nucleus accumbens and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus $D_3$ receptor antagonists are proposed to modulate psychotic symptoms such as hallucinations, delusions and thought disorder (Joyce J. N., Millan M. J., *Drug Discovery Today* (2005) 10:917-925). In addition, it has been reported that drug naive schizophrenic patients show altered levels of $D_3$ receptor expression (Gurevich E. V. et al., *Arch. Gen. Psychiatry* (1997) 54, 225-232) and dopamine release (Laruelle M., *Presentation at Institut de Recherches Internationales Servier Workshop on Schizophrenia: Pathological Bases and Mechanisms of Antipsychotic Action*, Chicago, Ill., 2000), indicating that a disturbed homeostasis of dopamine plays an important role in the etiology of schizophrenic symptoms.

The neurotransmitter serotonin (5-Hydroxytryptamine; 5-HT) is implicated in several psychiatric conditions including schizophrenia (Kandel E. R. et al. (eds.), *Principles of Neural Science* (2000) $3^{rd}$ edition, Appleton & Lange, Norwalk, Conn.). The involvement of serotonin in psychotic disorders is suggested by multiple studies which include treatment in humans with the psychotropic drug Lysergic acid (LSD; a serotonin agonist) which can induce schizophrenia-like symptoms such as hallucinations (Leikin J. B. et al., *Med. Toxicol. Adverse Drug Exp.* (1989) 4:324-350). Furthermore, altered brain distribution of serotonin receptors as well as an altered serotonergic tone, have been detected in schizophrenic patients (Harrison P. J., *Br. J. Psychiatry Suppl.* (1999) 38:12-22).

In mammals, serotonin exerts its biological activities through a family of 14 5-HT GPCRs. The 5-$HT_{2A}$ receptor is most prominently expressed in the prefrontal cortex and at lower levels in the basal ganglia and the hippocampus in human brain, and is coupled predominantly to the G-protein Gαq. Genetic linkage studies of a 5-$HT_{2A}$ polymorph to schizophrenia (Spurlock G. et al., *Mol. Psychiatry* (1998) 3:42-49), as well as responsiveness to antipsychotic drugs (Arran, M J. et al., *Lancet* (2000) 355:1615-1616), further suggest a role for the 5-$HT_{2A}$ receptor both in the treatment and pathology of psychosis. In addition, dopaminergic neurotransmission appears to be under the afferent regulation of the 5-$HT_{2A}$ receptor (Porras G. et al., *Neuropsychopharmaco-gy* (2002) 26:311-324). Overall 5-$HT_{2A}$ receptor antagonists are proposed to be suitable for the treatment of disorders associated with dysfunctional dopaminergic systems. Moreover, 5-$HT_{2A}$ receptor antagonism has been recognized as beneficial for the treatment of psychosis (de Angelis L., *Curr. Opin. Investig. Drugs* (2002) 3:106-112).

The $D_3$ and 5-$HT_{2A}$ receptors besides the mentioned psychotic disorders are further reported to be linked to other psychoses including paranoia and delusions (Reavill C. et al., *JPET* (2000) 294:1154-1165; Harrison P. J., *Br. J. Psychiatry Suppl.* (1999) 38:12-22), to drug dependency, abuse and withdrawal (Voxel S. R. et al., *J. Neurosci.* (2002) 22:9595-9603; Campos A. C. et al., *Soc. Neurosci. Abstr.*, (2003) 322:8; Ashby C. R. et al., *Synapse* (2003) 48:154-156), attention deficit hyperactivity disorders (ADHD) (Retz W. et al., *J. Neural. Transm.* (2003) 110:531-572; Levitan R. D. et al., *J. Affective Disorder* (2002) 71:229-233), as well as to anxiety and depression (Reavill C. et al., *JPET* (2000) 294:1154-1165; Drescher K. et al. *Am. Soc. Neurosci.* (2002) 894:6).

Currently used medications to treat schizophrenia, bipolar mania and other psychoses, include both typical ($D_2$/$D_3$ preferring) or the more recent atypicals, which exhibit polypharma-cology interacting at multiple receptors (e.g., $D_1$, $D_2$, $D_3$, $D_4$, 5-$HT_{1A}$, 5-$HT_{2A}$, 5-$HT_{2C}$, $H_1$, $M_1$, $M_2$, $M_4$, etc.)(Roth B. L. et al., *Nat. Rev. Drug Discov.* (2004) 3:353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems. Furthermore, patient compliance is compromised by prevalent side effects such as weight gain, extrapyramidal symptoms (EPS), and cardiovascular effects (Lieberman J. A. et al., *N. Engl. J. Med.* (2005) 353:1209-1223).

Antipsychotic drug treatment has frequently been complicated by serious side effects of widespread $D_2$ antagonism, notably an extrapyramidal or parkinsonian syndrome caused by antagonism of the dopaminergic projection from substantia nigra to corpus striatum. $D_2$ receptor blockade induces catalepsy and has been associated with negative effects against cognition. Also preferential blockade of $D_3$ vs. $D_2$ receptors, preserves and/or enhances cognitive function, and increases frontocortical cholinergic transmission. (Joyce J. N., Millan M. J., *Drug Discovery Today* (2005) 10:917-925, Moore N. A. et al., *European Journal of Pharmacology* (1993) 237:1-7; Barth V. N., *Typical and atypical antipsychotics: Relationships between rat in vivo dopamine D(2) receptor occupancy assessed using LC/MS and changes in neurochemistry and catalepsy*. Dissertation Indiana University (2006); Millan M. J. et al., *Fr. Journal of Pharmacology* and Experimental Therapeutics (2008) 324:1212-1226; Wiecki T. V. et al., Psychophannacology (2009) 204:265-277).

The typical antipsychotic agents on the market today display $D_2$ antagonism, and most have extrapyramidal side effects (EPS) such as pseudoparkinsonism and tardive dyskinesia (Howard H. R., Seeger T. F., Annual Reports in Medicinal Chemistry (1993) 28:39). It has been shown by selective binding experiments that $D_2$ receptors are more concentrated in the striatal regions of the brain, which are responsible for locomotor control than in the limbic regions which are responsible for thought processes. $D_3$ receptors are more concentrated in the limbic than in the striatal regions. It is therefore believed that selective $D_3$ ligands may relieve symptoms of schizophrenia without causing the EPS associated with blockade of $D_2$ receptors (Gackenheimer S. L. et al., J. Pharmacol. Exp. Ther. (1995) 274:1558, Belliotti T. R., Bioorg. Med. Chem. Lett. (1997) 7:2403).

SUMMARY OF THE INVENTION

The present invention provides dual modulators of the $5\text{-HT}_{2A}$ and $D_3$ receptors, their manufacture, pharmaceutical compositions containing them and their use as pharmaceuticals.

In particular, the present invention provides compounds of formula (I)

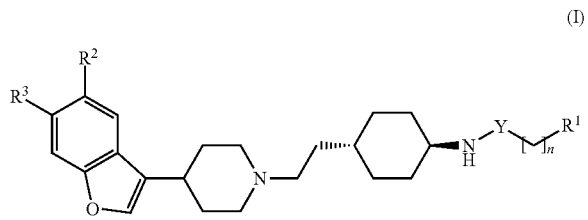

(I)

wherein $R^1$, $R^2$, $R^3$, n and Y are as described herein, and pharmaceutically acceptable salts and esters thereof.

The compounds of the invention and their pharmaceutically acceptable salts have high affinity and selectivity for both, the dopamine $D_3$ and serotonin $5\text{-HT}_{2A}$ receptors and are effective, alone or in combination with other drugs, in the treatment or prevention of psychotic disorders, as well as other diseases such as depression, anxiety, drug addiction, attention deficit hyperactivity disorders, dementia and memory impairment, while exhibiting fewer associated side effects.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkyl-aryl", "haloalkyl-heteroaryl", "arylalkyl-heterocycloalkyl", or "alkoxy-alkyl". The last member of the combination is a radical that is substituted by the other members of the combination in inverse order.

When indicating the number of substituents, the term "one or more" refers to the range from one substituent to the highest possible number of substitution, i.e. replacement of one hydrogen atom up to replacement of all hydrogen atoms by substituents.

The term "optional" or "optionally" denotes that a subsequently described event or circumstance may, but need not, occur and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen atom up to replacement of all hydrogen atoms by substituents.

The term "compound(s) of this invention" and "compound(s) of the present invention" refers to compounds of formula (I) and stereoisomers, tautomers, solvates, and salts (e.g., pharmaceutically acceptable salts) thereof.

It will be appreciated, that the compounds of present invention can be derivatized at functional groups to provide derivatives that are capable of conversion back to the parent compound in vivo. Physiologically acceptable and metabolically labile derivatives, which are capable of producing the parent compounds of present invention in vivo are also within the scope of this invention.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The term "pharmaceutically acceptable salts" denotes salts, which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "trans-configuration" denotes the configuration within a molecule, wherein a pair of substituents is attached on opposite sides of a stereoisomeric group.

The term "protecting group" denotes the group that selectively blocks a reactive site in a multifunctional compound such that a chemical reaction can be carried out selectively at another unprotected reactive site in the meaning conventionally associated with it in synthetic chemistry. Protecting groups can be removed at the appropriat point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting group.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "halo", "halogen", and "halide" are used interchangeably herein and denote fluoro, chloro, bromo, or iodo. Particular example of halogen is fluoro and chloro.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, or tert-butyl. Particular examples of alkyl are methyl, ethyl, n-propyl, iso-propyl, n-butyl, iso-butyl, and tert-butyl; most particularly methyl, ethyl, iso-propyl, iso-butyl and tert-butyl.

The term "alkenyl" denotes a monovalent linear or branched hydrocarbon group of 2 to 7 carbon atoms, in particular 2 to 4 carbon atoms, with at least one double bond. Examples of alkenyl include ethenyl, propenyl, prop-2-enyl, iso-propenyl, n-butenyl, iso-butenyl, and tert-butenyl. Particular examples of alkylene are n-propenyl and iso-butylene, more particularly prop-2-enyl and iso-butenyl.

The term "alkynyl" denotes a monovalent linear or branched hydrocarbon group of 2 to 7 carbon atoms, in particular from 2 to 4 carbon atoms, that contains one, two or three triple bonds. Examples of alkynyl include ethynyl, propynyl, prop-2-ynyl, isopropynyl, n-butynyl, and iso-butynyl. Aparticular example of alkynyl is propynyl, most particularly prop-1-ynyl.

The term "alkoxy" denotes a group of the formula —O—R', wherein R' is an alkyl group as defined herein. Examples of alkoxy moieties include methoxy, ethoxy, isopropoxy, and tert-butoxy. Particular examples of alkoxy are methoxy and tert-butoxy.

The term "haloalkyl" denotes an alkyl group as defined herein wherein at least one of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, and trifluoromethyl. The term "perhaloalkyl" denotes an alkyl group where all hydrogen atoms of the alkyl group have been replaced by the same or different halogen atoms. Particular examples of haloalkyl are trifluoromethyl and trifluoroethyl, most particularly trifluoromethyl.

The term "haloalkoxy" denotes an alkoxy group wherein at least one of the hydrogen atoms of the alkoxy group has been replaced by the same or different halogen atom, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, and trifluoromethoxy. The term "perhaloalkoxy" denotes an alkoxy group where all hydrogen atoms of the alkoxy group have been replaced by the same or different halogen atoms.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. "Bicyclic" means two saturated carbocycles that have one or more carbon atoms in common. Particular cycloalkyl groups are monocyclic. Examples for monocyclic cycloalkyl are cyclopropyl, cyclobutanyl, cyclopentyl, cyclohexyl or cycloheptyl.

Examples for bicyclic cycloalkyl are bicyclo[2.2.1]heptanyl and bicyclo[2.2.2]octanyl. Particular examples of cycloalkyl are cyclopropyl, cyclobutyl, cyclopentyl, and cyclohexyl; most particularly cyclopropyl and cyclohexyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "heterocycloalkyl" denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, and dihydropyranyl. Particular examples of heterocycloalkyl are oxetanyl, tetrahydrofuranyl, piperidinyl, tetrahydropyranyl, piperazinyl, morpholinyl, thiomorpholinyl, and dioxanyl—more particularly piperidinyl, tetrahydropyranyl, morpholinyl, and dioxanyl.

The term "heterocycloalkylalkyl" denotes an alkyl group wherein at least one of the hydrogen atoms of the alkyl group is replaced by a heterocycloalkyl group.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl, most particularly phenyl.

The term "aryl anellated to heterocycloalkyl" denotes an aryl group as defined herein and a heterocycloalkyl group as defined herein which are fused together sharing two adjacent ring atoms. Examples of aryl annellated to heterocycloalkyl include optionally substituted benzodioxolyl.

The term "heteroaryl" denotes a monovalent aromatic heterocyclic mono- or bicyclic ring system of 5 to 12 ring atoms, containing 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, and quinoxalinyl. Particular examples of heteroaryl are pyrrolyl, pyrazolyl, isoxazolyl, oxaziazolyl, thienyl, pyridinyl, pyrazinyl, quinolinyl, and benzoisoxazolyl, most particularly oxadiazolyl.

The term "oxo" denotes a divalent oxygen atom =O.

The term "alkylsulfonyl" denotes a group —SO$_2$—R', wherein R' is alkyl. Examples of alkylsulfonyl include methylsulfonyl, and ethylsulfonyl, particularly methylsulfonyl.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" (or "composition") denotes a mixture or solution comprising a therapeutically effective amount of an active pharmaceutical ingredient together with pharmaceutically acceptable excipients to be administered to a mammal, e.g., a human in need thereof.

The term "modulator" denotes a molecule that interacts with a target. The interactions include e.g. agonistic, antagonistic, or inverse agonistic activity.

The term "antagonist" denotes a compound that diminishes or prevents the action of another compound or receptor site as defined e.g. in Goodman and Gilman's "The Pharmacological Basis of Therapeutics, 7th ed." in page 35, Macmillan Publ. Company, Canada, 1985. In particular, antagonist refers to a compound that attenuates the effect of an agonist. A "competitive antagonist" binds to the same site as the agonist but does not activate it, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

The term "treating" or "treatment" of a disease state includes (1) preventing the disease state, i.e. causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

The term "subject" denotes a vertebrate. In certain embodiments, the vertebrate is a mammal Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In detail, the present invention provides compounds of formula (I)

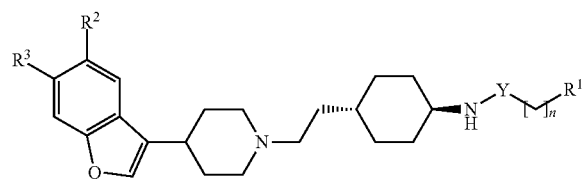

wherein
n is 0, 1, 2, 3 or 4;
Y is —C(O)— or —S(O)$_2$—;
R$^1$ is hydrogen, alkyl, alkenyl, alkynyl, haloalkyl, cycloalkyl, adamantyl, heterocycloalkyl, aryl, aryl anellated to heterocycloalkyl, heteroaryl, —NR$^6$R$^7$, hydroxy, alkoxy, or haloalkoxy; wherein alkyl, alkenyl, alkynyl, haloalkyl, alkoxy and haloalkoxy are each optionally substituted by one, two or three independent R$^4$; and
wherein cycloalkyl, adamantyl, heterocycloalkyl, aryl, aryl anellated to heterocycloalkyl, and heteroaryl are each optionally substituted by one, two or three independent R$^5$;
R$^2$ and R$^3$ are each independently hydrogen, halogen, cyano, alkyl, haloalkyl, hydroxy, alkoxy or haloalkoxy;
R$^4$ is cyano, cycloalkyl, heterocycloalkyl, aryl, heteroaryl, —C(O)NR$^6$R$^7$, —NR$^6$R$^7$, —NH(CO)-alkyl, hydroxy, alkoxy, haloalkoxy, oxo, or —S(O)$_2$R$^6$;
wherein cycloalkyl, heterocycloalkyl, aryl, and heteroaryl, are each optionally substituted by one, two or three independent R$^5$;
R$^5$ is halogen, cyano, alkyl, haloalkyl, cycloalkyl, heterocycloalkyl, aryl, heteroaryl, —C(O)NR$^6$R$^7$, —NR$^6$R$^7$, —NH(CO)-alkyl, hydroxy, alkoxy, haloalkoxy, oxo, or —S(O)$_2$R$^6$;
wherein cycloalkyl, heterocycloalkyl, aryl, and heteroaryl, are each optionally substituted by one, two or three substituents independently selected from halogen, cyano, alkyl, haloalkyl, hydroxy, alkoxy, haloalkoxy, and oxo;
R$^6$ and R$^7$ are each independently hydrogen, alkyl, haloalkyl, cycloalkyl, cycloalkylalkyl, heterocycloalkyl, heterocycloalkylalkyl, aryl, or heteroaryl;
and pharmaceutically acceptable salts and esters thereof.

Particular embodiments of present invention are compounds of formula (I) and pharmaceutically acceptable salts thereof and pharmaceutically acceptable esters thereof.

Further, it is to be understood that every embodiment relating to a specific residue n, Y, R$^1$, R$^2$, R$^3$, R$^4$, R$^5$, R$^6$, or R$^7$ as disclosed herein can be combined with any other embodiment relating to another residue n, Y, R$^1$, R$^2$, R$^3$, R$^4$, R$^5$, R$^6$, or R$^7$ as disclosed herein.

A particular embodiment of the present invention provides compounds of formula (I) wherein the two opposing substituents at the central cyclohexyl moiety of the molecular backbone, the amidyl residue and the piperidinyl-ethyl residue, are oriented in trans-configuration.

A particular embodiment of the present invention provides compounds of formula (I')

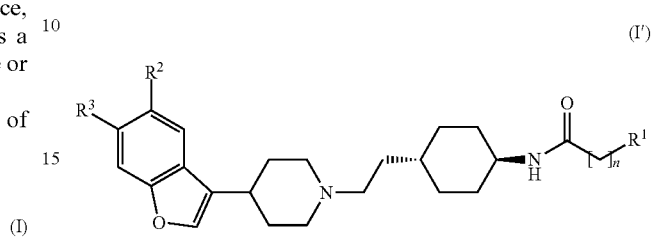

wherein n, R$^1$, R$^2$, and R$^3$ are as defined herein.

A particular embodiment of the present invention provides compounds of formula (I")

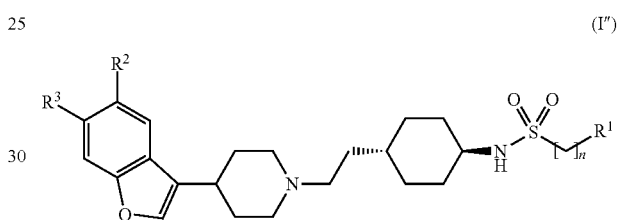

wherein n, R$^1$, R$^2$, and R$^3$ are as defined herein.

In a particular embodiment of the compound of formula (I), n is 0.

In a particular embodiment of the compound of formula (I), n is 1.

In a particular embodiment of the compound of formula (I), n is 2.

In a particular embodiment of the compound of formula (I), n is 3.

In a particular embodiment of the compound of formula (I), n is 4.

In a particular embodiment of the compound of formula (I), n is 0, 1 or 2.

In a particular embodiment of the compound of formula (I), Y is —C(O)—.

In a particular embodiment of the compound of formula (I), Y is —S(O)$_2$—.

In a particular embodiment of the compound of formula (I), R$^1$ hydrogen, alkyl, alkenyl, alkynyl, haloalkyl, cycloalkyl, adamantyl, heterocycloalkyl, aryl, aryl anellated to heterocycloalkyl, heteroaryl, —NR$^6$R$^7$, hydroxy, alkoxy, or haloalkoxy; and wherein alkyl, and haloalkyl, are each optionally substituted by one, two or three independent R$^4$; wherein cycloalkyl, aryl, and heteroaryl are each optionally substituted by one, two or three independent R$^5$.

In a particular embodiment of the compound of formula (I), R$^1$ is hydrogen, methyl, methyl substituted by methoxy, n-propyl, n-propyl substituted by hydroxy, iso-propyl, iso-propyl substituted by hydroxy, n-butyl, tert-butyl, n-propenyl, iso-butenyl, propynyl, trifluoromethyl, trifluoroethyl, trifluoroethyl substituted by hydroxy, cyclopropyl, cyclopropyl substituted by fluoro, cyclopropyl substituted by hydroxy, cyclobutyl, cyclohexyl, cyclohexyl substituted by tert-butyl, cyclohexyl substituted by trifluoromethyl, cyclohexyl substituted by methoxy, adamantyl, oxetanyl, tetrahydrofuranyl, tetrahydropyranyl, dioxanyl, phenyl, phenyl substituted by $R^8$, benzodioxolyl, isoxazolyl, isoxazolyl substituted by methyl, thienyl, thienyl substituted by methyl-sulfonyl, pyridinyl, pyridinyl substituted by methyl, pyridinyl substituted by morpholinyl, pyrazinyl, pyrazinyl substituted by morpholinyl, quinolinyl, benzoisoxazolyl, —N(methyl)$_2$, hydroxy, or methoxy; wherein $R^8$ is selected from fluoro, chloro, cyano, methyl, ethyl, iso-propyl, iso-butyl, tert-butyl, trifluoromethyl, cyclopropyl, cyclohexyl, piperidinyl, methyl-piperazinyl, morpholinyl, dioxo-thiomorpholinyl, phenyl, pyrrolyl, pyrazolyl, methyl-oxadiazolyl, pyridinyl, tert-butoxy, or methyl-sulfonyl.

In a particular embodiment of the compound of formula (I), $R^1$ is cyclohexyl, cyclohexyl substituted by tert-butyl, tetrahydropyranyl, dioxanyl, methoxy, phenyl, or phenyl substituted by a substituent selected from the list of ethyl, iso-propyl, iso-butyl, tert-butyl, trifluoromethyl, cyclopropyl, piperidinyl, morpholinyl, methyl-oxadiazolyl, and tert-butoxy.

In a particular embodiment of the compound of formula (I), $R^2$ is hydrogen.

In a particular embodiment of the compound of formula (I), $R^3$ is hydrogen.

In a particular embodiment of the compound of formula (I), $R^2$ and $R^3$ are each hydrogen.

In a particular embodiment of the compound of formula (I), $R^4$ is cyano, —C(O)—NR$^6$R$^7$, hydroxy, alkoxy, or —S(O)$_2$R$^6$.

In a particular embodiment of the compound of formula (I), $R^4$ is cyano, —C(O)N(methyl)$_2$, hydroxy, methoxy, or methyl-sulfonyl.

In a particular embodiment of the compound of formula (I), $R^5$ is halogen, cyano, alkyl, haloalkyl, cycloalkyl, heterocycloalkyl, aryl, heteroaryl, hydroxy, alkoxy, or alkylsulfonyl; and wherein heterocycloalkyl, and heteroaryl are each optionally substituted by one, two or three substituents independently selected from alkyl, and oxo.

In a particular embodiment of the compound of formula (I), $R^5$ is fluoro, chloro, cyano, methyl, ethyl, iso-propyl, iso-butyl, tert-butyl, trifluoromethyl, cyclopropyl, cyclohexyl, piperidinyl, methyl-piperazinyl, morpholinyl, dioxo-thiomorpholinyl, phenyl, pyrrolyl, pyrazolyl, methyl-oxadiazolyl, pyridinyl, hydroxy, methoxy, tert-butoxy, or methyl-sulfonyl.

In a particular embodiment of the compound of formula (I), $R^5$ is ethyl, iso-propyl, iso-butyl, tert-butyl, trifluoromethyl, cyclopropyl, piperidinyl, morpholinyl, methyl-oxadiazolyl, or tert-butoxy.

In a particular embodiment of the compound of formula (I), $R^6$ and $R^7$ are each independently selected from alkyl.

In a particular embodiment of the compound of formula (I), $R^6$ and $R^7$ are each methyl.

A particular embodiment of the present invention provides compounds of formula (I) as described in the examples as individual compounds as well as pharmaceutically acceptable salts as well as pharmaceutically acceptable esters thereof. Furthermore, the substituents as found in the specific examples described below individually constitute separate particular embodiments of the present invention.

Particular compounds of formula (I) of present invention are those selected from the group consisting of:

trans-N-{4-[2-(4-Benzofuran-3-yl-piperidin-1-yl)-ethyl]-cyclohexyl}-acetamide;
trans-N-{4-[2-(4-Benzofuran-3-yl-piperidin-1-yl)-ethyl]-cyclohexyl}-3-methoxy-propionamide;
Tetrahydro-pyran-4-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-(tetrahydro-pyran-4-yl)-acetamide;
trans-N-{4-[2-(4-Benzofuran-3-yl-piperidin-1-yl)-ethyl]-cyclohexyl}-propionamide;
trans-N-{4-[2-(4-Benzofuran-3-yl-piperidin-1-yl)-ethyl]-cyclohexyl}-2-methoxy-acetamide;
trans-N-{4-[2-(4-Benzofuran-3-yl-piperidin-1-yl)-ethyl]-cyclohexyl}-2-methanesulfonyl-acetamide;
trans-N-{4-[2-(4-Benzofuran-3-yl-piperidin-1-yl)-ethyl]-cyclohexyl}-(RS)-2-[1,4]dioxan-2-yl-acetamide;
trans-N-{4-[2-(4-Benzofuran-3-yl-piperidin-1-yl)-ethyl]-cyclohexyl}-benzamide;
trans-N-{4-[2-(4-Benzofuran-3-yl-piperidin-1-yl)-ethyl]-cyclohexyl}-2-(3-methyl-isoxazol-5-yl)-acetamide;
trans-N-{4-[2-(4-Benzofuran-3-yl-piperidin-1-yl)-ethyl]-cyclohexyl}-2-hydroxy-acetamide;
trans-N-{4-[2-(4-Benzofuran-3-yl-piperidin-1-yl)-ethyl]-cyclohexyl}-3,3,3-trifluoro-propionamide;
trans-N-{4-[2-(4-Benzofuran-3-yl-piperidin-1-yl)-ethyl]-cyclohexyl}-4-morpholin-4-yl-benzamide;
trans-N-{4-[2-(4-Benzofuran-3-yl-piperidin-1-yl)-ethyl]-cyclohexyl}-isobutyramide;
trans-N-{4-[2-(4-Benzofuran-3-yl-piperidin-1-yl)-ethyl]-cyclohexyl}-3-methyl-butyramide;
trans-N-{4-[2-(4-Benzofuran-3-yl-piperidin-1-yl)-ethyl]-cyclohexyl}-2-hydroxy-2-methyl-propionamide;
(RS)-Tetrahydro-furan-3-carboxylic acid trans-{4-[2-(4-benzofuran-3-yl-piperidin-1-yl)-ethyl-cyclohexyl}-amide;
(RS)-Tetrahydro-furan-2-carboxylic acid trans-{4-[2-(4-benzofuran-3-yl-piperidin-1-yl)-ethyl]-cyclohexyl}-amide;
Quinoline-4-carboxylic acid trans-{4-[2-(4-benzofuran-3-yl-piperidin-1-yl)-ethyl]-cyclohexyl}-amide;
Cyclobutanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-3-hydroxy-propionamide;
1-Hydroxy-cyclopropanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-cyano-acetamide;
trans-N-{4-[2-(4-Benzofuran-3-yl-piperidin-1-yl)-ethyl]-cyclohexyl}-4-fluoro-benzamide;
trans-N-{4-[2-(4-Benzofuran-3-yl-piperidin-1-yl)-ethyl]-cyclohexyl}-2-cyclopropyl-acetamide;
Tetrahydro-pyran-3-carboxylic acid trans-{4-[2-(4-benzofuran-3-yl-piperidin-1-yl)-ethyl]-cyclohexyl}-amide;
Cyclopropanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2,2-dimethyl-propionamide;
trans-N-{4-[2-(4-Benzofuran-3-yl-piperidin-1-yl)-ethyl]-cyclohexyl}-2-(tetrahydro-furan-2-yl)-acetamide;
2,2-Difluoro-cyclopropanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-(RS)-2-methyl-butyramide;
trans-N-{4-[2-(4-Benzofuran-3-yl-piperidin-1-yl)-ethyl]-cyclohexyl}-(RS)-3,3,3-trifluoro-2-hydroxy-propionamide;
trans-N-{4-[2-(4-Benzofuran-3-yl-piperidin-1-yl)-ethyl]-cyclohexyl}-butyramide;
trans-N-{4-[2-(4-Benzofuran-3-yl-piperidin-1-yl)-ethyl]-cyclohexyl}-3-hydroxy-3-methyl-butyramide;
trans-N-{4-[2-(4-Benzofuran-3-yl-piperidin-1-yl)-ethyl]-cyclohexyl}-(R)-4,4,4-trifluoro-3-hydroxy-butyramide;

trans-N-{4-[2-(4-Benzofuran-3-yl-piperidin-1-yl)-ethyl]-cyclohexyl}-methanesulfonamide;
Ethanesulfonic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-methyl-benzenesulfonamide;
trans-N-{4-[2-(4-Benzofuran-3-yl-piperidin-1-yl)-ethyl]-cyclohexyl}-2,2,2-trifluoro-acetamide;
trans-N-{4-[2-(4-Benzofuran-3-yl-piperidin-1-yl)-ethyl]-cyclohexyl}-3,3-dimethyl-butyramide;
3-Methyl-isoxazole-5-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-N',N'-dimethyl-succinamide;
N'-(trans-4-{2-[4-(benzofuran-3-yl)-piperidin-1-yl]-ethyl}-cyclohexyl)-N,N-dimethylsulfamide;
trans-N-{4-[2-(4-Benzofuran-3-yl-piperidin-1-yl)-ethyl]-cyclohexyl}-4,4,4-trifluoro-butyramide;
4-Methyl-pentanoic acid trans-{4-[2-(4-benzofuran-3-yl-piperidin-1-yl)-ethyl]-cyclohexyl}-amide;
(R)-3-Hydroxy-pentanoic acid trans-{4-[2-(4-benzofuran-3-yl-piperidin-1-yl)-ethyl]-cyclohexyl}-amide;
(S)-3-Hydroxy-pentanoic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-cyclobutyl-acetamide;
trans-N-{4-[2-(4-Benzofuran-3-yl-piperidin-1-yl)-ethyl]-cyclohexyl}-4-chloro-benzamide;
trans-N-{4-[2-(4-Benzofuran-3-yl-piperidin-1-yl)-ethyl]-cyclohexyl}-4-trifluoromethyl-benzamide;
trans-N-{4-[2-(4-Benzofuran-3-yl-piperidin-1-yl)-ethyl]-cyclohexyl}-4-piperidin-1-yl-benzamide;
trans-N-{4-[2-(4-Benzofuran-3-yl-piperidin-1-yl)-ethyl]-cyclohexyl}-3,3-dimethoxy-propionamide;
3-Methyl-but-2-enoic acid trans-{4-[2-(4-benzofuran-3-yl-piperidin-1-yl)-ethyl]-cyclohexyl}-amide;
(E)-Pent-3-enoic acid trans-{4-[2-(4-benzofuran-3-yl-piperidin-1-yl)-ethyl]-cyclohexyl}-amide;
But-2-ynoic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-formamide;
Pentanoic acid trans-{4-[2-(4-benzofuran-3-yl-piperidin-1-yl)-ethyl]-cyclohexyl}-amide;
Benzo[1,3]dioxole-5-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-pyrazol-1-yl-benzamide;
trans-N-{4-[2-(4-Benzofuran-3-yl-piperidin-1-yl)-ethyl]-cyclohexyl}-4-tert-butyl-benzamide;
trans-N-{4-[2-(4-Benzofuran-3-yl-piperidin-1-yl)-ethyl]-cyclohexyl}-4-(5-methyl-[1,2,4]oxadiazol-3-yl)-benzamide;
trans-N-{4-[2-(4-Benzofuran-3-yl-piperidin-1-yl)-ethyl]-cyclohexyl}-4-(4-methyl-piperazin-1-yl)-benzamide;
Biphenyl-4-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-pyridin-3-yl-benzamide;
trans-N-{4-[2-(4-Benzofuran-3-yl-piperidin-1-yl)-ethyl]-cyclohexyl}-6-morpholin-4-yl-nicotinamide;
trans-N-{4-[2-(4-Benzofuran-3-yl-piperidin-1-yl)-ethyl]-cyclohexyl}-4-(1,1-dioxo-1λ6-thiomorpholin-4-yl)-benzamide;
5-Morpholin-4-yl-pyrazine-2-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-pyrrol-1-yl-benzamide;
trans-N-{4-[2-(4-Benzofuran-3-yl-piperidin-1-yl)-ethyl]-cyclohexyl}-6-methyl-nicotinamide;
trans-N-{4-[2-(4-Benzofuran-3-yl-piperidin-1-yl)-ethyl]-cyclohexyl}-4-cyano-benzamide;
trans-N-{4-[2-(4-Benzofuran-3-yl-piperidin-1-yl)-ethyl]-cyclohexyl}-4-tert-butoxy-benzamide;
trans-N-{4-[2-(4-Benzofuran-3-yl-piperidin-1-yl)-ethyl]-cyclohexyl}-2-trans-(4-methoxy-cyclohexyl)-acetamide;
Quinoline-6-carboxylic acid trans-{4-[2-(4-benzofuran-3-yl-piperidin-1-yl)-ethyl]-cyclohexyl}-amide;
trans-2-Benzo[1,3]dioxol-5-yl-N-{4-[2-(4-benzofuran-3-yl-piperidin-1-yl)-ethyl]-cyclohexyl}-acetamide;
5-Methanesulfonyl-thiophene-2-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-oxetan-3-yl-acetamide;
4-tert-Butyl-cyclohexanecarboxylic acid trans-{4-[2-(4-benzofuran-3-yl-piperidin-1-yl)-ethyl]-cyclohexyl}-amide;
Adamantane-1-carboxylic acid trans-{4-[2-(4-benzofuran-3-yl-piperidin-1-yl)-ethyl]-cyclohexyl}-amide;
4-Trifluoromethyl-cyclohexanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-isobutyl-benzamide;
trans-N-{4-[2-(4-Benzofuran-3-yl-piperidin-1-yl)-ethyl]-cyclohexyl}-4-ethyl-benzamide;
trans-N-{4-[2-(4-Benzofuran-3-yl-piperidin-1-yl)-ethyl]-cyclohexyl}-4-cyclohexyl-benzamide;
trans-N-{4-[2-(4-Benzofuran-3-yl-piperidin-1-yl)-ethyl]-cyclohexyl}-4-isopropyl-benzamide;
trans-N-{4-[2-(4-Benzofuran-3-yl-piperidin-1-yl)-ethyl]-cyclohexyl}-4-cyclopropyl-benzamide;
trans-2-Benzo[d]isoxazol-3-yl-N-{4-[2-(4-benzofuran-3-yl-piperidin-1-yl)-ethyl]-cyclohexyl}-acetamide;
trans-N-{4-[2-(4-Benzofuran-3-yl-piperidin-1-yl)-ethyl]-cyclohexyl}-4-methanesulfonyl-benzamide;
trans-N-{4-[2-(4-Benzofuran-3-yl-piperidin-1-yl)-ethyl]-cyclohexyl}-2,4-dichloro-benzamide; and
trans-N-{4-[2-(4-Benzofuran-3-yl-piperidin-1-yl)-ethyl]-cyclohexyl}-4-tert-butyl-benzenesulfonamide; and
pharmaceutically acceptable salts and esters thereof.
Particular compounds of formula (I) of present invention are those selected from the group consisting of:
trans-N-{4-[2-(4-Benzofuran-3-yl-piperidin-1-yl)-ethyl]-cyclohexyl}-3-methoxy-propionamide;
trans-N-{4-[2-(4-Benzofuran-3-yl-piperidin-1-yl)-ethyl]-cyclohexyl}-2-(tetrahydro-pyran-4-yl)-acetamide;
trans-N-{4-[2-(4-Benzofuran-3-yl-piperidin-1-yl)-ethyl]-cyclohexyl}-2-methoxy-acetamide;
trans-N-{4-[2-(4-Benzofuran-3-yl-piperidin-1-yl)-ethyl]-cyclohexyl}-(RS)-2-[1,4]dioxan-2-yl-acetamide;
trans-N-{4-[2-(4-Benzofuran-3-yl-piperidin-1-yl)-ethyl]-cyclohexyl}-4-morpholin-4-yl-benzamide;
trans-N-{4-[2-(4-Benzofuran-3-yl-piperidin-1-yl)-ethyl]-cyclohexyl}-4-trifluoromethyl-benzamide;
trans-N-{4-[2-(4-Benzofuran-3-yl-piperidin-1-yl)-ethyl]-cyclohexyl}-4-piperidin-1-yl-benzamide;
trans-N-{4-[2-(4-Benzofuran-3-yl-piperidin-1-yl)-ethyl]-cyclohexyl}-4-tert-butyl-benzamide;
trans-N-{4-[2-(4-Benzofuran-3-yl-piperidin-1-yl)-ethyl]-cyclohexyl}-4-(5-methyl-[1,2,4]oxadiazol-3-yl)-benzamide;

trans-N-{4-[2-(4-Benzofuran-3-yl-piperidin-1-yl)-ethyl]-cyclohexyl}-4-tert-butoxy-benzamide;

4-tert-Butyl-cyclohexanecarboxylic acid trans-{4-[2-(4-benzofuran-3-yl-piperidin-1-yl)-ethyl]-cyclohexyl}-amide;

trans-N-{4-[2-(4-Benzofuran-3-yl-piperidin-1-yl)-ethyl]-cyclohexyl}-4-isobutyl-benzamide;

trans-N-{4-[2-(4-Benzofuran-3-yl-piperidin-1-yl)-ethyl]-cyclohexyl}-4-ethyl-benzamide;

trans-N-{4-[2-(4-Benzofuran-3-yl-piperidin-1-yl)-ethyl]-cyclohexyl}-4-isopropyl-benzamide; and trans-N-{4-[2-(4-Benzofuran-3-yl-piperidin-1-yl)-ethyl]-cyclohexyl}-4-cyclopropyl-benzamide; and pharmaceutically acceptable salts and esters thereof.

The invention further provides a process for the manufacture of compounds of formula (I) as defined above comprising:

a) the reaction of a compound of formula (V)

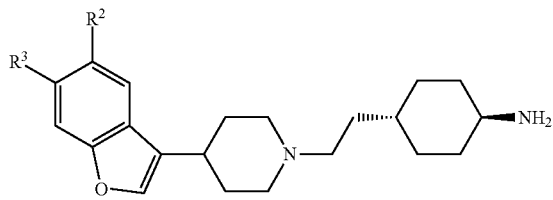

(V)

with a compound of formula $R^1(CH_2)_nC(O)OH$, $R^1(CH_2)_nC(O)OR$ or $R^1(CH_2)_nS(O)_2Cl$, wherein n, $R^1$, $R^2$, and $R^3$ are as defined above and R is alkyl; or b) the reaction of a compound of formula (II)

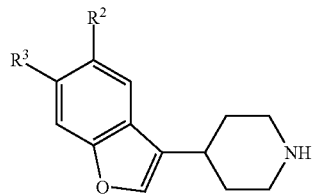

(II)

with a compound of formula (VI)

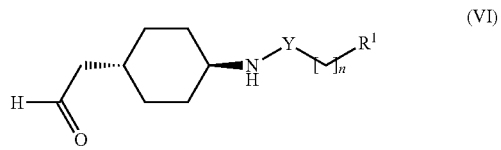

(VI)

wherein n, Y, $R^1$, $R^2$, and $R^3$ are as defined above.

Particularly, compounds of formula (I) can be prepared following standard methods in accordance with Schemes 1 or 2.

According to Scheme 1, in a first step, a compound of formula (II) is reacted with an aldehyde of formula (III) under reductive amination conditions such as for example the use of sodium triacetoxyborohydride (Na(AcO)₃BH) in a solvent such as 1,2-dichloroethane in the presence of methanol (MeOH) or an acid such as acetic acid (AcOH) to give a compound of formula (IV). The amino moiety of aldehyde (III) is protected with an amino-protecting group such as a Boc moiety. In a second step, compounds of formula (IV) are deprotected to give compounds of formula (V). In such cases where the amino-protecting group is a Boc functionality, compounds of formula (IV) can be reacted with an acid as for example HCl in an appropriate solvent mixture such as ethylacetate (AcOEt) and MeOH to give primary amines isolated as the HCl salts (V).

Compounds of formula (V) can be reacted in a third step with a number of different nucleophiles to obtain compounds of formula (I). For instance reaction of compounds of formula (V) with a carboxylic acid of general structure $R^1(CH_2)_nC(O)OH$ in the presence of a coupling agent such as O-(benzotriazol-1-yl)-N,N,N',N'-tetramethyluronium tetrafluoroborate (TBTU) and a base such as Hunig's base (N,N-Diisopropylethylamine, DIPEA) in a solvent such as dimethylformamide (DMF) leads to compounds of formula (I'). In some instances carboxylic acids of general structure $R^1(CH_2)_n C(O)OH$ or their salts can be prepared by saponification of an ester of formula $R^1(CH_2)_nC(O)OR$, wherein R is alkyl, with a reagent such as a base like LiOH or mild reagents like potassium trimethylsilanolate (KOSiMe₃) in a solvent such as dichloromethane (DCM) followed by full evaporation of all solvent and direct use of the crude in the amide coupling step described above to obtain compounds of formula (I').

Scheme 1

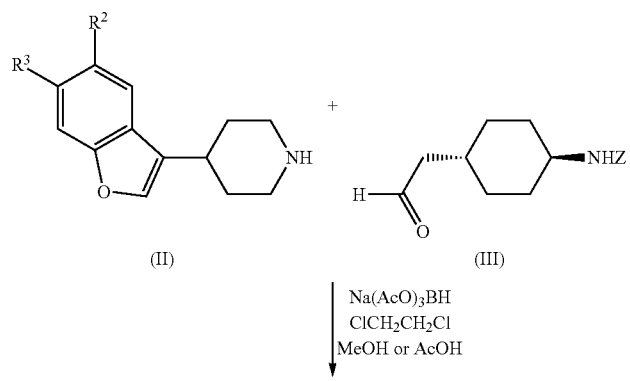

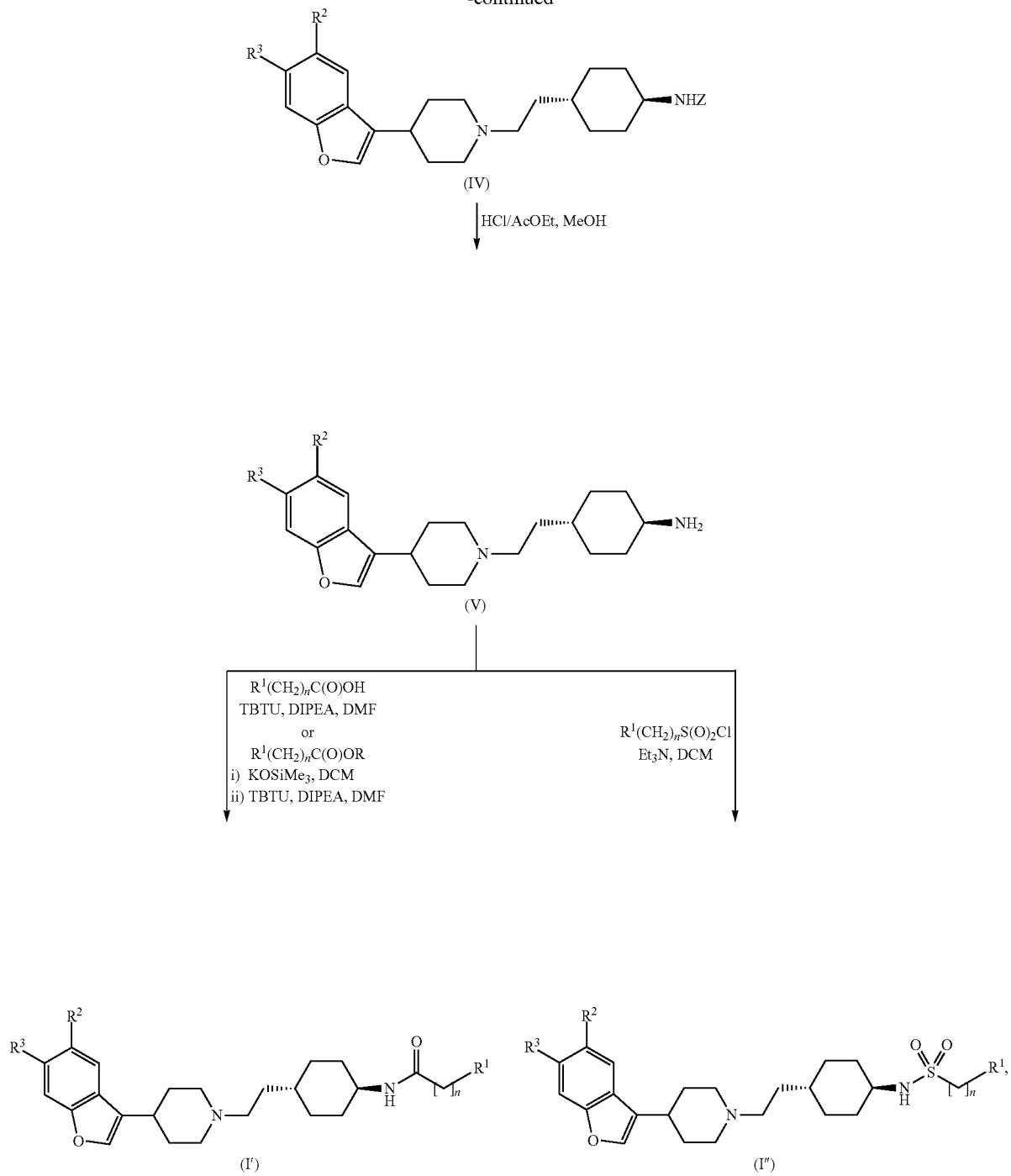

wherein n, $R^1$, $R^2$, and $R^3$ are as defined above, Z is an amino-protecting group and R is alkyl.

Yet in another instance, compounds of formula (V) can be reacted with an appropriate reagent of general structure $R^1(CH_2)_nS(O)_2Cl$ in the presence of a base such as triethylamine ($Et_3N$) in a solvent such as DCM to obtain compounds of formula (I").

Derivatization at the primary amine does not necessarily need to be carried out in a last step, but can occur already prior to the reductive amination step, thus avoiding the use of an amino-protecting group. According to Scheme 2, the reductive amination of a compound of formula (II) with an aldehyde of formula (VI) under conditions well known to the person skilled in the art, will directly lead to an amide of formula (I). An example for appropriate conditions for this step is the use of $Na(AcO)_3BH$ in a solvent such as 1,2-dichloroethane in the presence or not of MeOH or an acid such as AcOH. Methods to generate compounds of formula (VI) have been described (e.g. WO 2007/093540).

Scheme 2

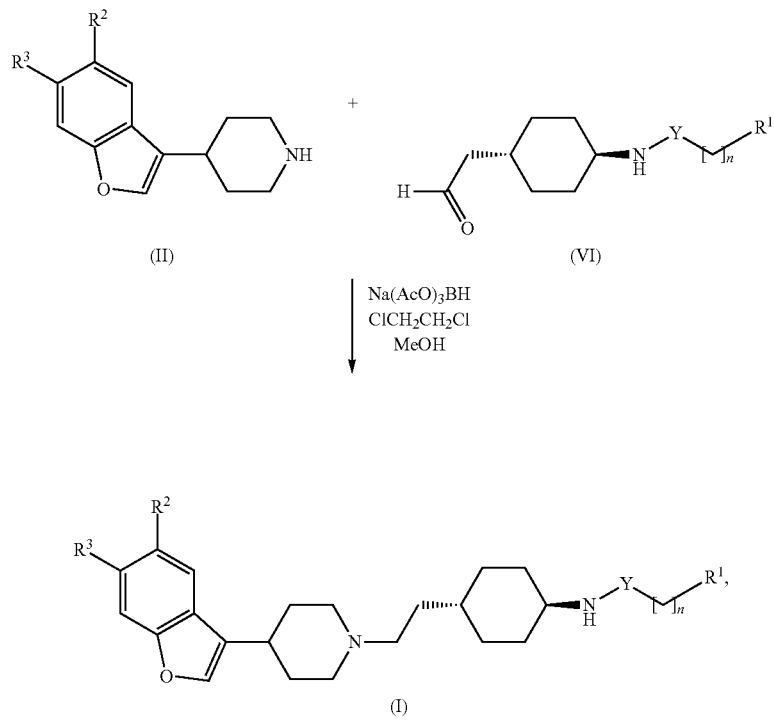

wherein n, Y, R¹, R², and R³ are as defined above.

According to Scheme 3, compounds of formulae (II) can be prepared from the corresponding 3-bromobenzofurane compounds of formula (VII) and commercially available tert-butyl 4-(4,4,5,5-tetramethyl-1,3,2-dioxaborolan-2-yl)-5,6-dihydropyridine-1(2H)-carboxylate of formula (VIII) or similar boronic derivative, wherein Z is an amino-protecting group, particularly Boc by a cross coupling reaction to tert-butyl 4-(benzofuran-3-yl)-5,6-dihydropyridine-1(2H)-carboxylate (IX), subsequent de-protection and hydrogenation.

According to Scheme 3, compounds of formula (II) can be obtained from compounds of formula (VII) by cross-coupling with a compound of formula (VIII) or similar boronic derivative, wherein Z is an amino-protecting group, particularly Boc. Most particular compound of formula (VIII) is commercially available tert-butyl 4-(4,4,5,5-tetramethyl-1,3,2-dioxaborolan-2-yl)-5,6-dihydropyridine-1(2H)-carboxylate. The coupling between the compound of formula (VII) and the compound of formula (VIII) is performed under conditions well known to the person skilled in the art to obtain a compound of formula (IX), particularly to obtain tert-butyl 4-(benzofuran-3-yl)-5,6-dihydropyridine-1(2H)-carboxylate, for instance under Suzuki conditions using a catalyst such as palladium (II) acetate in presence of a ligand, particularly triphenylphosphine, in the presence of a base, particularly potassium bicarbonate, in a solvent, particularly 1,2-dimethoxyethane. Other coupling conditions are well known to person skilled in the art. Compounds of formula (IX), wherein Z is an amino-protecting group, particularly Boc, can be deprotected with an acid, particularly HCl, in an appropriate solvent mixture, particularly dioxane and MeOH, followed by hydrogenation of the double bond using Pd/C to obtain the desired benzofurane piperidines of formula (II).

Scheme 3

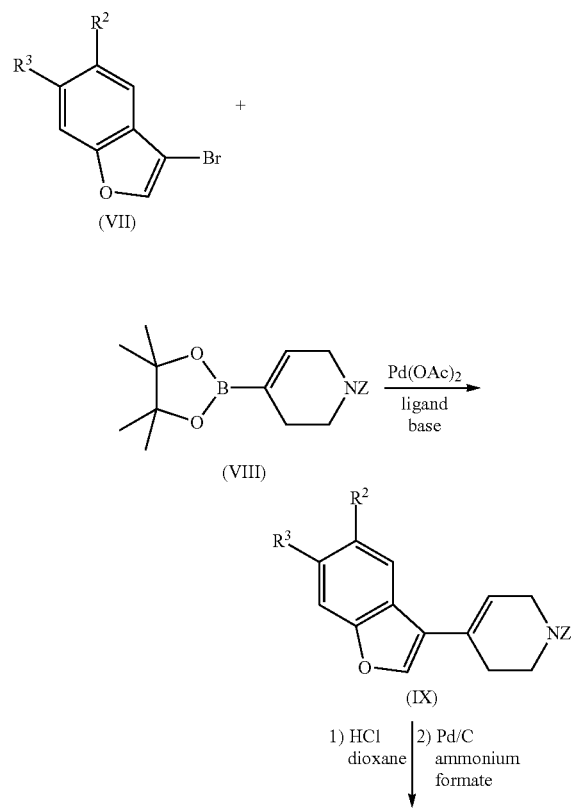

-continued

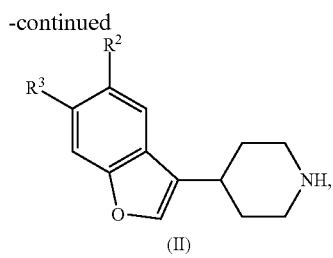

(II)

wherein $R^2$, and $R^3$ are as defined above, and Z is an amino-protecting group.

The corresponding salts of compounds of formula (I) with acids can be obtained by standard methods known to the person skilled in the art, e.g. by dissolving the compound of formula (I) in a suitable solvent such as e.g. dioxan or tetrahydrofuran (THF) and adding an appropriate amount of the corresponding acid. The products can usually be isolated by filtration or by chromatography.

The conversion of compounds of formula (I) into pharmaceutically acceptable esters can be carried out e.g. by treatment of a suitable hydroxy-group present in the molecule with a suitable carboxylic acid using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU).

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

The present invention also provides compounds of formula (I) as defined above, when prepared by a process as described above.

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention can be administered in any convenient administrative form, e.g., tablets, powders, capsules, solutions, dispersions, suspensions, syrups, sprays, suppositories, gels, emulsions, patches, etc. Such compositions can comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.1 to 1000 mg per person of a compound of formula (I) should be appropriate, although the above upper limit can also be exceeded when necessary.

An example of a suitable oral dosage form is a tablet containing about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution can be filtered, e.g., using a 0.2 μm filter, to remove impurities and contaminants.

As described above, the novel compounds of the present invention and their pharmaceutically acceptable salts and esters possess valuable pharmacological properties and have been found to be dual modulators of the $5\text{-HT}_{2A}$ and $D_3$ receptors. The compounds of the present invention can therefore be used, either alone or in combination with other drugs, for the treatment or prevention of diseases, which are modulated by ligands of the $5\text{-HT}_{2A}$ or $D_3$ receptors. These diseases include, but are not limited to psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

The invention therefore also provides pharmaceutical compositions comprising a compound as defined above and a pharmaceutically acceptable excipient.

The invention likewise embraces compounds as described above for use as therapeutically active substances, especially as therapeutically active substances for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

In another embodiment, the invention provides a method for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions, which method comprises administering a compound as defined above to a human being or animal.

The invention also embraces the use of compounds as defined above for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

The invention also provides the use of compounds as described above for the preparation of medicaments for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions. Such medicaments comprise a compound as described above.

Particularly, compounds of present invention can be used in the treatment or prevention of psychotic disorders including schizophrenia as well as positive, negative and/or cognitive symptoms associated with schizophrenia.

The invention will be more fully understood by reference to the following examples. They should not, however, be construed as limiting the scope of the invention.

Intermediates

Intermediate A: trans-4-[2-(4-Benzofuran-3-yl-piperidin-1-yl)-ethyl]-cyclohexylamine dihydrochloride

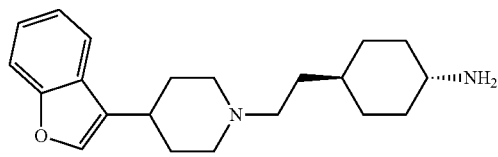 [SMILES: N[C@H]1CC[C@H](CCN2CCC(c3coc4ccccc34)CC2)CC1]

Step A

A mixture of commercially available 3-bromobenzofurane (2.50 g, 12.7 mmol) and commercially available tert-butyl 4-(4,4,5,5-tetramethyl-1,3,2-dioxaborolan-2-yl)-5,6-dihydropyridine-1(2H)-carboxylate (4.32 g, 14.0 mmol) in 1,2-dimethoxyethane (85 ml) and 2M sodium carbonate solution (21.1 ml, 42.3 mmol) was purged with argon in an ultrasonic bath during 5 min. Then triphenylphosphine (666 mg, 2.54 mmol) and palladium(II)acetate (285 mg, 1.27 mmol) were added and the reaction mixture was allowed to stir at 85° C. for 17 h. The reaction mixture was cooled to room temperature, poured into water (30 ml) and extracted with diethyl ether (2×120 ml). The combined organic layers were washed with brine (60 ml), dried (MgSO4) and evaporated. The crude product (5.78 g) was further purified by flash chromatography on silica gel (heptane/ethyl acetate 4:1) to yield tert-butyl 4-(benzofuran-3-yl)-5,6-dihydropyridine-1(2H)-carboxylate as a yellow oil (2.06 g, 54%), MS (ISP) m/z=300.2 [(M+H)$^+$].

Step B

To a stirred solution of tert-butyl 4-(benzofuran-3-yl)-5,6-dihydropyridine-1(2H)-carboxylate (2.06 g, 6.88 mmol) in dichloromethane (50 ml) was added at room temperature hydrochloric acid solution (4M in dioxane, 25.8 ml, 103 mmol) and the reaction mixture was allowed to stir for 2 h. The reaction mixture was diluted with dioxane (25 ml), the precipitate was collected by filtration, washed with dioxane and dried to yield 4-(benzofuran-3-yl)-1,2,3,6-tetrahydropyridine hydrochloride as off-white solid (1.37 g, 85%), MS (ISP) m/z=200.2 [(M+H)$^-$], mp 276° C.

Step C

A stirred mixture of 4-(benzofuran-3-yl)-1,2,3,6-tetrahydropyridine hydrochloride (1.57 g, 6.66 mmol), palladium on carbon (10%, 0.35 g, 0.33 mmol), ammonium formate (2.1 g, 33 3 mmol) and MeOH (61 ml) was heated at reflux conditions for 1 h, cooled to RT, filtrated and evaporated. The residue was diluted with ice-water (20 ml) and 3M NaOH (10 ml) and extracted with dichloromethane/methanol 9:1 (4×50 ml). The combined organic layers were washed with brine (1×25 ml), dried (MgSO4) and evaporated. The crude product (1.37 g) was purified by flash chromatography on silica gel (dichloromethane/methanol/NH4OH 65:10:1) to yield 4-(benzofuran-3-yl)-piperidine as a light yellow oil (1.1 g, 82%), MS (ISP) m/z=202.3 [(M+H)$^+$].

Step D

To a stirred solution of 4-(benzofuran-3-yl)-piperidine (1.1 g, 5.47 mmol) in dichloromethane (31 ml) was added at room temperature commercially available trans-tert-butyl-4-(2-oxoethyl)-cyclohexylcarbamate (1.86 g, 6.56 mmol) and triethylamnie (1.11 g, 1.52 ml, 10.9 mmol) and the solution was allowed to stir for 30 min. Sodium triacetoxyboron hydride (2.09 g, 9.84 mmol) was added step wise and the mixture was allowed to stir for 16 h at room temperature. The solution was poured into saturated sodium bicarbonate solution (20 ml) and extracted with dichloromethane (2×40 ml). The combined organic layers were washed with saturated sodium bicarbonate solution (20 ml), dried (MgSO4) and evaporated. The crude material (3.05 g) was purified by flash chromatography on silica gel (dichloromethane/MeOH 2-6%) to yield trans-{4-[2-(4-benzofuran-3-yl-piperidin-1-yl)-ethyl]-cyclohexyl}-carbamic acid tert-butyl ester as a white semisolid (2.31 g, 99%), MS (ISP) m/z=427.4 [(M+H)$^+$].

Step E

To a mixture of trans-{4-[2-(4-benzofuran-3-yl-piperidin-1-yl)-ethyl]-cyclohexyl}-carbamic acid tert-butyl ester (2.3 g, 5.39 mmol) in dichloromethane (40 ml) was added at room temperature hydrochloric acid solution (4M in dioxane, 20.2 ml, 80.9 mmol) and the mixture was allowed to stir for 2 h, diethyl ether (50 ml) was added and the mixture was allowed to stir for 30 min at room temperature. The precipitate was collected by filtration, washed with diethyl ether and dried to yield the title compound as a white solid (1.89 g, 88%), MS (ISP) m/z=327.4 [(M+H)⁻], mp 339° C.

EXAMPLES

Example 1 trans-N-{4-[2-(4-Benzofuran-3-yl-piperidin-1-yl)-ethyl]-cyclohexyl}-acetamide

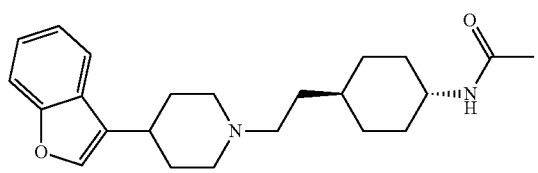 [SMILES: CC(=O)N[C@H]1CC[C@H](CCN2CCC(c3coc4ccccc34)CC2)CC1]

To a stirred mixture of trans-4-[2-(4-benzofuran-3-yl-piperidin-1-yl)-ethyl]-cyclohexylamine dihydrochloride (intermediate A) (100 mg, 0.25 mmol) in DMF (3 ml) was added N,N-diisopropylethylamine (113 mg, 150 µl, 0.88 mmol), acetic acid (22.6 mg, 21.5 µl, 376 µmol) and TBTU (121 mg, 376 µmol). The mixture was allowed to stir at room temperature for 16 h, poured into ice/water (5 ml) and 1N NaOH (5 ml) and extracted with dichloromethane (2×20 ml). The combined organic layers were washed with brine (10 ml), dried (MgSO4) and evaporated. The crude material was further purified by flash chromatography on silica gel (dichloromethane/MeOH/NH4OH 150:10:1) and trituration from dichloromethane (1 ml) and heptane (5 ml) for 30 min. The precipitate was collected by filtration, washed with heptane and dried to yield the title compound as a white solid (39 mg, 42%), MS (ISP) m/z=369.3 [(M+H)⁺], mp 162° C.

Example 2 trans-N-{4-[2-(4-Benzofuran-3-yl-piperidin-1-yl)-ethyl]-cyclohexyl}-3-methoxy-propionamide

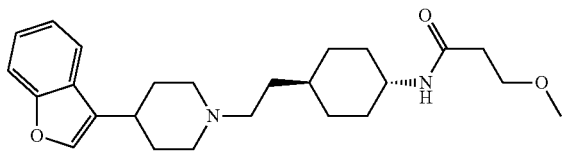 [SMILES: COCCC(=O)N[C@H]1CC[C@H](CCN2CCC(c3coc4ccccc34)CC2)CC1]

The title compound, white solid (51 mg, 50%), MS (ISP) m/z=413.5 [(M+H)⁺], mp 136° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 3-methoxy-propionic acid.

Example 3

Tetrahydro-pyran-4-carboxylic acid trans-{4-[2-(4-benzofuran-3-yl-piperidin-1-yl)-ethyl]-cyclohexyl}-amide

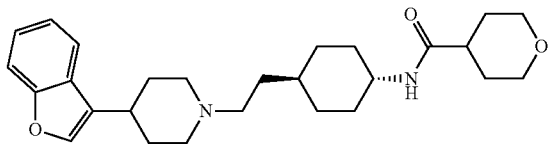 [SMILES: O=C(N[C@H]1CC[C@H](CCN2CCC(c3coc4ccccc34)CC2)CC1)C1CCOCC1]

The title compound, white solid (66 mg, 60%), MS (ISP) m/z=439.4 [(M+H)⁺], mp 175° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and tetrahydro-pyran-4-carboxylic acid.

Example 4 trans-N-{4-[2-(4-Benzofuran-3-yl-piperidin-1-yl)-ethyl]-cyclohexyl}-2-(tetrahydro-pyran-4-yl)-acetamide

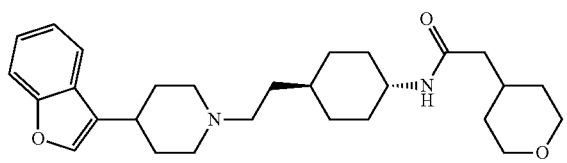 [SMILES: O=C(CC1CCOCC1)N[C@H]1CC[C@H](CCN2CCC(c3coc4ccccc34)CC2)CC1]

The title compound, white solid (58 mg, 51%), MS (ISP) m/z=453.4 [(M+H)⁺], mp 175° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-(tetrahydro-pyran-4-yl)-acetamide.

Example 5 trans-N-{4-[2-(4-Benzofuran-3-yl-piperidin-1-yl)-ethyl]-cyclohexyl}-propionamide

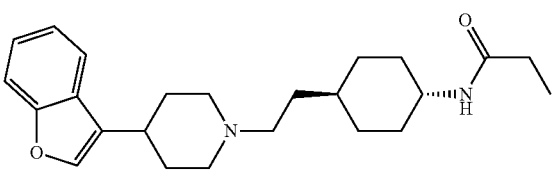 [SMILES: CCC(=O)N[C@H]1CC[C@H](CCN2CCC(c3coc4ccccc34)CC2)CC1]

The title compound, yellow solid (61 mg, 64%), MS (ISP) m/z=383.4 [(M+H)⁺], mp 162° C., was prepared in accordance with the general method of example 1 from trans-4-[2-

(4-benzofuran-3-yl-piperidin-1-yl)-ethyl]-cyclohexylamine dihydrochloride (intermediate A) (100 mg, 0.25 mmol) and propionic acid.

Example 6 trans-N-{4-[2-(4-Benzofuran-3-yl-piperidin-1-yl)-ethyl]-cyclohexyl}-2-methoxy-acetamide

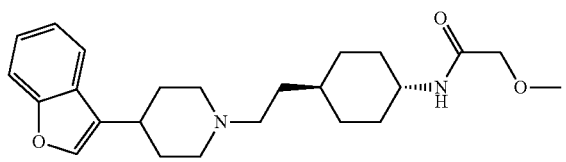

The title compound, white solid (59 mg, 59%), MS (ISP) m/z=399.3 [(M+H)$^+$], mp 115° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-methoxy-acetic acid.

Example 7 trans-N-{4-[2-(4-Benzofuran-3-yl-piperidin-1-yl)-ethyl]-cyclohexyl}-2-methanesulfonyl-acetamide

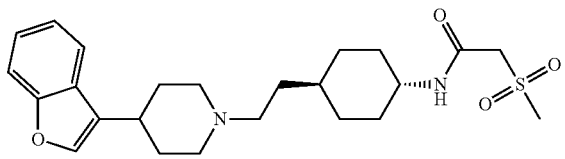 [SMILES: CS(=O)(=O)CC(=O)N[C@H]1CC[C@H](CCN2CCC(c3coc4ccccc34)CC2)CC1]

The title compound, white solid (79 mg, 71%), MS (ISP) m/z=447.3 [(M+H)$^+$], mp 187° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-methanesulfonyl-acetic acid.

Example 8 trans-N-{4-[2-(4-Benzofuran-3-yl-piperidin-1-yl)-ethyl]-cyclohexyl}-(RS)-2-[1,4]dioxan-2-yl-acetamide

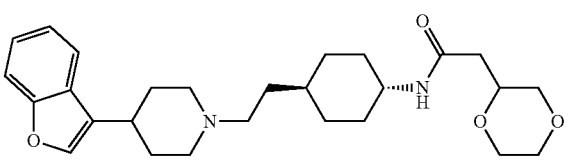 [SMILES: O=C(CC1COCCO1)N[C@H]1CC[C@H](CCN2CCC(c3coc4ccccc34)CC2)CC1]

The title compound, white solid (60 mg, 53%), MS (ISP) m/z=455.3 [(M+H)$^+$], mp 172° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and (RS)-2-[1,4]dioxan-2-yl-acetic acid.

Example 9 trans-N-{4-[2-(4-Benzofuran-3-yl-piperidin-1-yl)-ethyl]-cyclohexyl}-benzamide

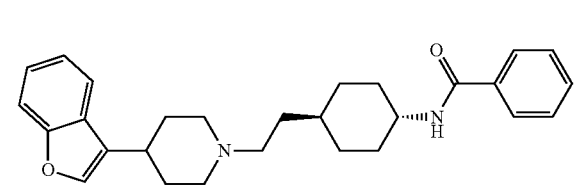 [SMILES: O=C(N[C@H]1CC[C@H](CCN2CCC(c3coc4ccccc34)CC2)CC1)c1ccccc1]

The title compound, light yellow solid (65 mg, 60%), MS (ISP) m/z=431.5 [(M+H)$^+$], mp 189° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and benzoic acid.

Example 10 trans-N-{4-[2-(4-Benzofuran-3-yl-piperidin-1-yl)-ethyl]-cyclohexyl}-2-(3-methyl-isoxazol-5-yl)-acetamide

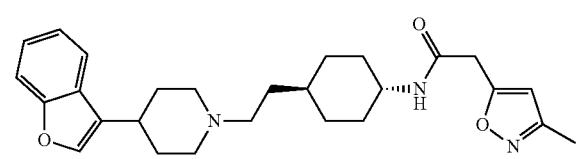 [SMILES: Cc1cc(CC(=O)N[C@H]2CC[C@H](CCN3CCC(c4coc5ccccc45)CC3)CC2)on1]

The title compound, off-white solid (84 mg, 74%), MS (ISP) m/z=450.3 [(M+H)$^+$], mp 165° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-(3-methyl-isoxazol-5-yl)-acetic acid.

Example 11 trans-N-{4-[2-(4-Benzofuran-3-yl-piperidin-1-yl)-ethyl]-cyclohexyl}-2-hydroxy-acetamide

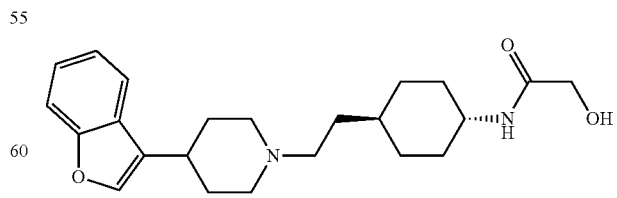

The title compound, off-white solid (70 mg, 73%), MS (ISP) m/z=385.4 [(M+H)$^+$], mp 161° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-hydroxy-acetic acid.

Example 12 trans-N-{4-[2-(4-Benzofuran-3-yl-piperidin-1-yl)-ethyl]-cyclohexyl}-3,3,3-trifluoro-propionamide

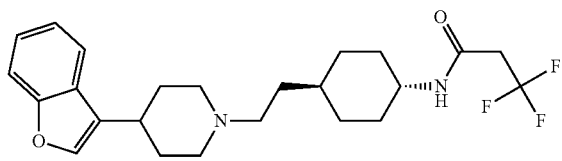

The title compound, off-white solid (84 mg, 77%), MS (ISP) m/z=437.3 [(M+H)$^+$], mp 182° C., was prepared in accordance with the general method of example 1 from trans-4-[2-(4-benzofuran-3-yl-piperidin-1-yl)-ethyl]-cyclohexy-lamine dihydrochloride (intermediate A) (100 mg, 0.25 mmol) and 3,3,3-trifluoro-propionic acid.

Example 13 trans-N-{4-[2-(4-Benzofuran-3-yl-piperidin-1-yl)-ethyl]-cyclohexyl}-4-morpholin-4-yl-benzamide

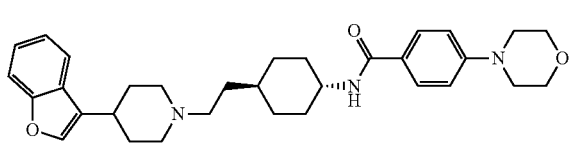

The title compound, light yellow solid (103 mg, 80%), MS (ISP) m/z=516.3 [(M+H)$^+$], mp 249° C., was prepared in accordance with the general method of example 1 from trans-4-[2-(4-benzofuran-3-yl-piperidin-1-yl)-ethyl]-cyclohexy-lamine dihydrochloride (intermediate A) (100 mg, 0.25 mmol) and 4-morpholin-4-yl-benzoic acid.

Example 14 trans-N-{4-[2-(4-Benzofuran-3-yl-piperidin-1-yl)-ethyl]-cyclohexyl}-isobutyramide

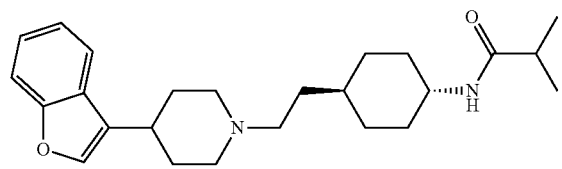

The title compound, off-white solid (70 mg, 70%), MS (ISP) m/z=397.3 [(M+H)$^+$], mp 173° C., was prepared in accordance with the general method of example 1 from trans-4-[2-(4-benzofuran-3-yl-piperidin-1-yl)-ethyl]-cyclohexy-lamine dihydrochloride (intermediate A) (100 mg, 0.25 mmol) and isobutyric acid.

Example 15 trans-N-{4-[2-(4-Benzofuran-3-yl-piperidin-1-yl)-ethyl]-cyclohexyl}-3-methyl-butyramide

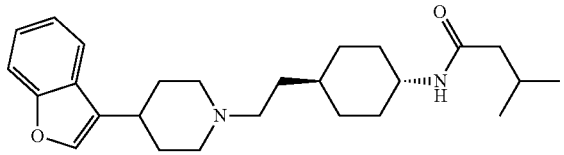

The title compound, off-white solid (74 mg, 72%), MS (ISP) m/z=411.5 [(M+H)$^+$], mp 182° C., was prepared in accordance with the general method of example 1 from trans-4-[2-(4-benzofuran-3-yl-piperidin-1-yl)-ethyl]-cyclohexy-lamine dihydrochloride (intermediate A) (100 mg, 0.25 mmol) and 3-methyl-butyric acid.

Example 16 trans-N-{4-[2-(4-Benzofuran-3-yl-piperidin-1-yl)-ethyl]-cyclohexyl}-2-hydroxy-2-methyl-propionamide

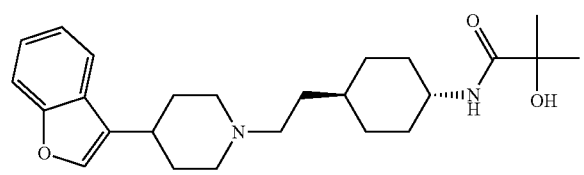 [SMILES: CC(C)(O)C(=O)N[C@H]1CC[C@H](CCN2CCC(c3coc4ccccc34)CC2)CC1]

The title compound, white solid (65 mg, 63%), MS (ISP) m/z=413.4 [(M+H)$^+$], mp 169° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-hydroxy-2-methyl-propionamide.

Example 17

(RS)-Tetrahydro-furan-3-carboxylic acid trans-{4-[2-(4-benzofuran-3-yl-piperidin-1-yl)-ethyl]-cyclo-hexyl}-amide

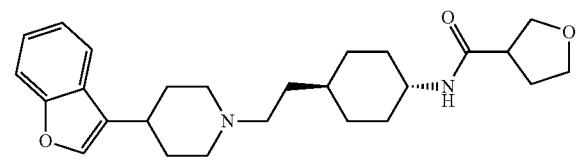 [SMILES: O=C(N[C@H]1CC[C@H](CCN2CCC(c3coc4ccccc34)CC2)CC1)C1CCOC1]

The title compound, light yellow solid (79 mg, 75%), MS (ISP) m/z=425.2 [(M+H)$^+$], mp 183° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and (RS)-tetrahydro-furan-3-carboxylic acid.

Example 18

(RS)-Tetrahydro-furan-2-carboxylic acid trans-{4-[2-(4-benzofuran-3-yl-piperidin-1-yl)-ethyl]-cyclohexyl}-amide

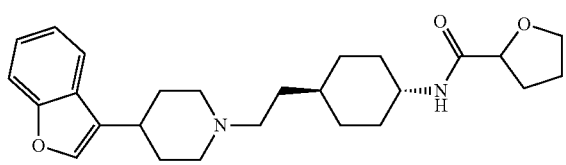 [SMILES: O=C(N[C@H]1CC[C@H](CCN2CCC(c3coc4ccccc34)CC2)CC1)C1CCCO1]

The title compound, off-white solid (74 mg, 70%), MS (ISP) m/z=425.3 [(M+H)⁺], mp 132° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and (RS)-tetrahydro-furan-2-carboxylic acid.

Example 19

Quinoline-4-carboxylic acid trans-{4-[2-(4-benzofuran-3-yl-piperidin-1-yl)-ethyl]-cyclohexyl}-amide

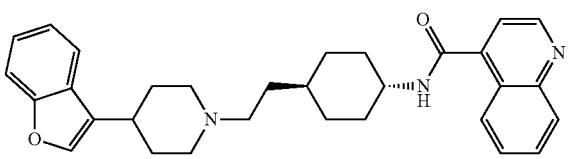 [SMILES: O=C(N[C@H]1CC[C@H](CCN2CCC(c3coc4ccccc34)CC2)CC1)c1ccnc2ccccc12]

The title compound, yellow solid (106 mg, 88%), MS (ISP) m/z=482.3 [(M+H)⁺], mp 169° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and quinoline-4-carboxylic acid.

Example 20

Cyclobutanecarboxylic acid trans-{4-[2-(4-benzofuran-3-yl-piperidin-1-yl)-ethyl]-cyclohexyl}-amide

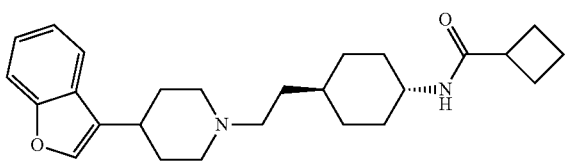 [SMILES: O=C(N[C@H]1CC[C@H](CCN2CCC(c3coc4ccccc34)CC2)CC1)C1CCC1]

The title compound, off-white solid (70 mg, 69%), MS (ISP) m/z=409.4 [(M+H)⁺], mp 180° C., was prepared in accordance with the general method of example 1 from trans-4-[2-(4-benzofuran-3-yl-piperidin-1-yl)-ethyl]-cyclohexy-lamine dihydrochloride (intermediate A) (100 mg, 0.25 mmol) and cyclobutanecarboxylic acid.

Example 21 trans-N-{4-[2-(4-Benzofuran-3-yl-piperidin-1-yl)-ethyl]-cyclohexyl}-3-hydroxy-propionamide

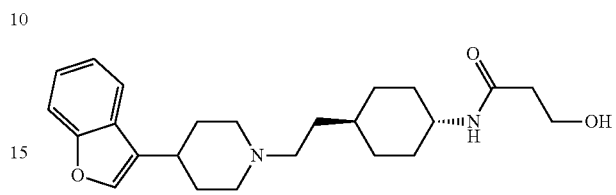

The title compound, off-white solid (20 mg, 20%), MS (ISP) m/z=399.3 [(M+H)⁺], mp 148° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 3-hydroxy-propionic acid.

Example 22

1-Hydroxy-cyclopropanecarboxylic acid trans-{4-[2-(4-benzofuran-3-yl-piperidin-1-yl)-ethyl]-cyclohexyl}-amide

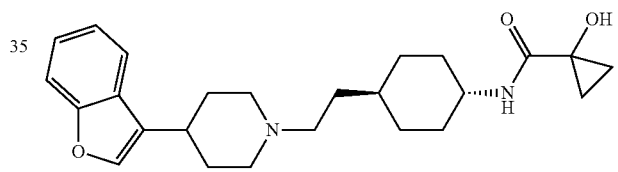

The title compound, white solid (67 mg, 65%), MS (ISP) m/z=411.3 [(M+H)⁺], mp 200° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 1-hydroxy-cyclopropanecarboxylic acid.

Example 23 trans-N-{4-[2-(4-Benzofuran-3-yl-piperidin-1-yl)-ethyl]-cyclohexyl}-2-cyano-acetamide

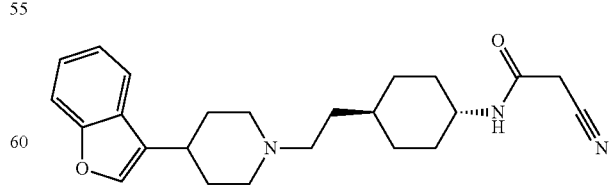

The title compound, off-white solid (50 mg, 51%), MS (ISP) m/z=394.3 [(M+H)⁺], mp 186° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-cyano-acetic acid.

Example 24 trans-N-{4-[2-(4-Benzofuran-3-yl-piperidin-1-yl)-ethyl]-cyclohexyl}-4-fluoro-benzamide

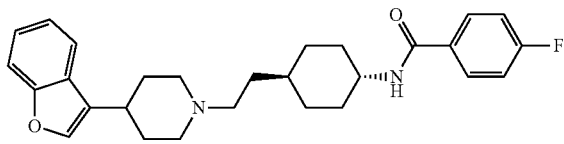 [SMILES: O=C(N[C@H]1CC[C@H](CCN2CCC(c3coc4ccccc34)CC2)CC1)c1ccc(F)cc1]

The title compound, light yellow solid (92 mg, 82%), MS (ISP) m/z=449.3 [(M+H)+], mp 193° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-fluoro-benzoic acid.

Example 25 trans-N-{4-[2-(4-Benzofuran-3-yl-piperidin-1-yl)-ethyl]-cyclohexyl}-2-cyclopropyl-acetamide

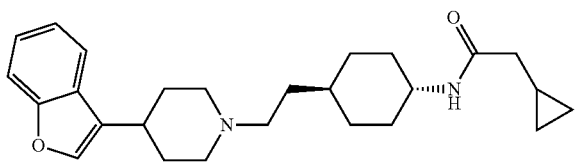 [SMILES: O=C(CC1CC1)N[C@H]1CC[C@H](CCN2CCC(c3coc4ccccc34)CC2)CC1]

The title compound, light yellow solid (74 mg, 73%), MS (ISP) m/z=409.4 [(M+H)+], mp 165° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-cyclopropyl-acetic acid.

Example 26

Tetrahydro-pyran-3-carboxylic acid trans-{4-[2-(4-benzofuran-3-yl-piperidin-1-yl)-ethyl]-cyclohexyl}-amide

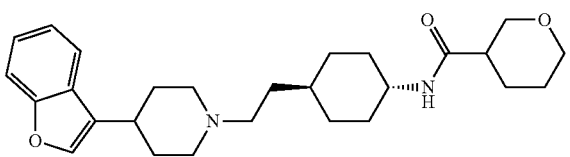 [SMILES: O=C(N[C@H]1CC[C@H](CCN2CCC(c3coc4ccccc34)CC2)CC1)C1CCCOC1]

The title compound, light yellow solid (78 mg, 71%), MS (ISP) m/z=439.3 [(M+H)+], mp 188° C., was prepared in accordance with the general method of example 1 from trans-4-[2-(4-benzofuran-3-yl-piperidin-1-yl)-ethyl]-cyclohexy-lamine dihydrochloride (intermediate A) (100 mg, 0.25 mmol) and (RS)-tetrahydro-pyran-3-carboxylic acid.

Example 27

Cyclopropanecarboxylic acid trans-{4-[2-(4-benzofuran-3-yl-piperidin-1-yl)-ethyl]-cyclohexyl}-amide

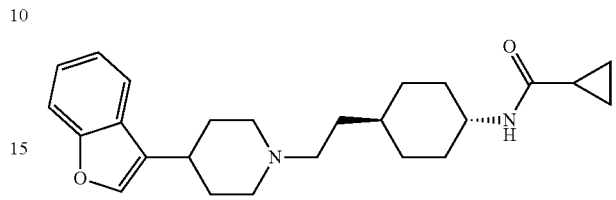

The title compound, white solid (73 mg, 74%), MS (ISP) m/z=395.3 [(M+H)+], mp 204° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and cyclopropanecarboxylic acid.

Example 28 trans-N-{4-[2-(4-Benzofuran-3-yl-piperidin-1-yl)-ethyl]-cyclohexyl}-2,2-dimethyl-propionamide

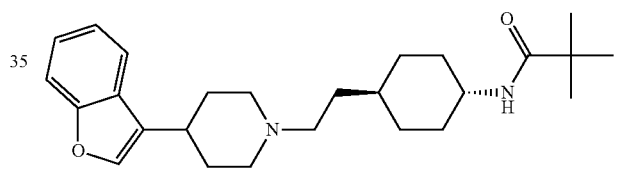

The title compound, white solid (76 mg, 74%), MS (ISP) m/z=411.5 [(M+H)+], mp 157° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2,2-dimethyl-propionic acid.

Example 29 trans-N-{4-[2-(4-Benzofuran-3-yl-piperidin-1-yl)-ethyl]-cyclohexyl}-2-(tetrahydro-furan-2-yl)-acetamide

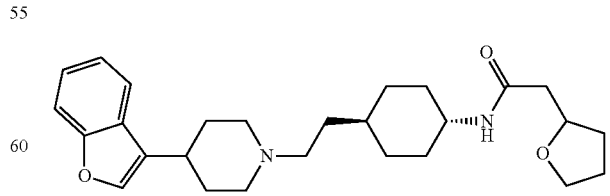

The title compound, off-white solid (62 mg, 56%), MS (ISP) m/z=439.4 [(M+H)+], mp 149° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and rac-(tetrahydro-furan-2-yl)-acetic acid.

Example 30

2,2-Difluoro-cyclopropanecarboxylic acid trans-{4-[2-(4-benzofuran-3-yl-piperidin-1-yl)-ethyl]-cyclohexyl}-amide

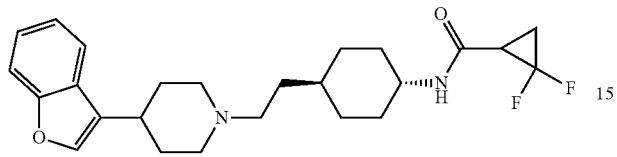

The title compound, light brown solid (81 mg, 75%), MS (ISP) m/z=431.4 [(M+H)⁺], mp 189° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2,2-difluoro-cyclopropane-carboxylic acid.

Example 31 trans-N-{4-[2-(4-Benzofuran-3-yl-piperidin-1-yl)-ethyl]-cyclohexyl}-(RS)-2-methyl-butyramide

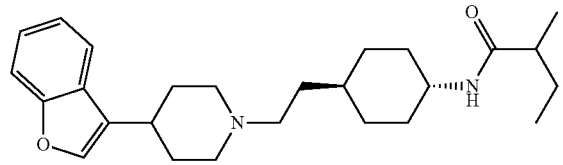 [SMILES: CCC(C)C(=O)N[C@H]1CC[C@H](CCN2CCC(c3coc4ccccc34)CC2)CC1]

The title compound, off-white solid (77 mg, 75%), MS (ISP) m/z=411.4 [(M+H)⁺], mp 172° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and (RS)-2-methyl-butyric acid.

Example 32 trans-N-{4-[2-(4-Benzofuran-3-yl-piperidin-1-yl)-ethyl]-cyclohexyl}-(RS)-3,3,3-trifluoro-2-hydroxy-propionamide

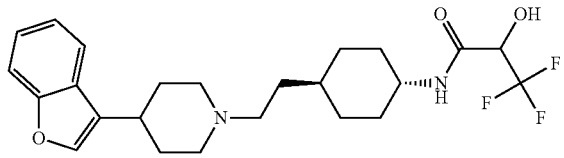 [SMILES: O=C(N[C@H]1CC[C@H](CCN2CCC(c3coc4ccccc34)CC2)CC1)C(O)C(F)(F)F]

The title compound, light yellow solid (91 mg, 81%), MS (ISP) m/z=453.3 [(M+H)⁺], mp 206° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and (RS)-3,3,3-trifluoro-2-hydroxy-propionic acid.

Example 33 trans-N-{4-[2-(4-Benzofuran-3-yl-piperidin-1-yl)-ethyl]-cyclohexyl}-butyramide

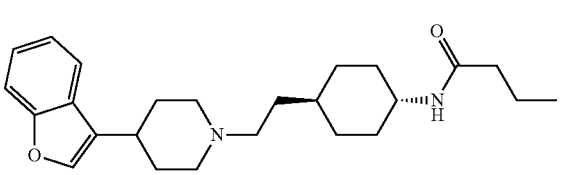 [SMILES: CCCC(=O)N[C@H]1CC[C@H](CCN2CCC(c3coc4ccccc34)CC2)CC1]

The title compound, off-white solid (60 mg, 60%), MS (ISP) m/z=397.3 [(M+H)⁺], mp 155° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and butyric acid.

Example 34 trans-N-{4-[2-(4-Benzofuran-3-yl-piperidin-1-yl)-ethyl]-cyclohexyl}-3-hydroxy-3-methyl-butyramide

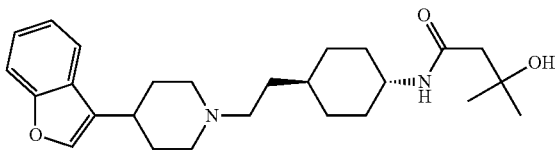 [SMILES: CC(C)(O)CC(=O)N[C@H]1CC[C@H](CCN2CCC(c3coc4ccccc34)CC2)CC1]

The title compound, light yellow solid (59 mg, 55%), MS (ISP) m/z=427.3 [(M+H)⁺], mp 150° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 3-hydroxy-3-methyl-butyric acid.

Example 35 trans-N-{4-[2-(4-Benzofuran-3-yl-piperidin-1-yl)-ethyl]-cyclohexyl}-(R)-4,4,4-trifluoro-3-hydroxy-butyramide

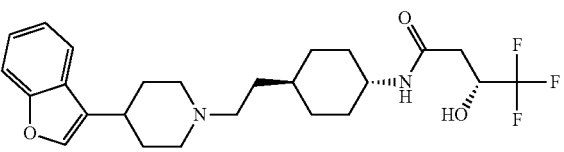 [SMILES: O=C(C[C@@H](O)C(F)(F)F)N[C@H]1CC[C@H](CCN2CCC(c3coc4ccccc34)CC2)CC1]

The title compound, off-white solid (79 mg, 68%), MS (ISP) m/z=467.2 [(M+H)⁺], mp 166° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and (R)-4,4,4-trifluoro-3-hydroxy-butyric acid.

Example 36 trans-N-{4-[2-(4-Benzofuran-3-yl-piperidin-1-yl)-ethyl]-cyclohexyl}-methanesulfonamide

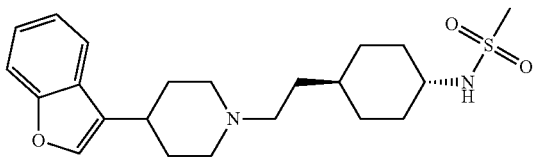 [SMILES: CS(=O)(=O)N[C@H]1CC[C@H](CCN2CCC(c3coc4ccccc34)CC2)CC1]

To a stirred mixture of trans-4-[2-(4-benzofuran-3-yl-piperidin-1-yl)-ethyl]-cyclohexylamine dihydrochloride (intermediate A) (100 mg, 0.25 mmol) in dichloromethane (1.5 ml) was added at room temperature triethylamine (88.7 mg, 122 μl, 0.876 mmol) and methanesulfonyl chloride (43 mg, 29.2 μl, 376 μmol). The mixture was allowed to stir at room temperature for 18 h, and was afterwards evaporated. The crude material was further purified by flash chromatography on silica gel (dichloromethane/MeOH/NH4OH 150:10:1) and trituration with dichloromethane (1 ml) and heptane (5 mL) for 30 min to yield the title compound as a white solid (62 mg, 61%), MS (ISP) m/z=405.4 [(M+H)$^+$], mp 142° C.

Example 37

Ethanesulfonic acid trans-{4-[2-(4-benzofuran-3-yl-piperidin-1-yl)-ethyl]-cyclohexyl}-amide

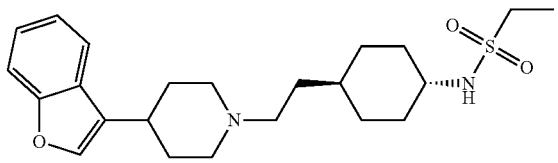 [SMILES: CCS(=O)(=O)N[C@H]1CC[C@H](CCN2CCC(c3coc4ccccc34)CC2)CC1]

The title compound, white solid (54 mg, 51%), MS (ISP) m/z=419.3 [(M+H)$^+$], mp 153° C., was prepared in accordance with the general method of example 36 from trans-4-[2-(4-benzofuran-3-yl-piperidin-1-yl)-ethyl]-cyclohexylamine dihydrochloride (intermediate A) (100 mg, 0.25 mmol) and ethanesulfonyl chloride.

Example 38 trans-N-{4-[2-(4-Benzofuran-3-yl-piperidin-1-yl)-ethyl]-cyclohexyl}-4-methyl-benzenesulfonamide

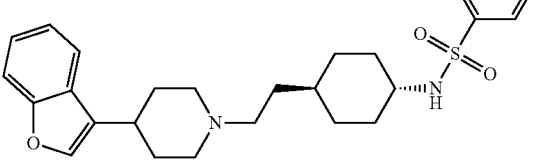

The title compound, light brown solid (79 mg, 66%), MS (ISP) m/z=481.3 [(M+H)$^+$], mp 149° C., was prepared in accordance with the general method of example 36 from trans-4-[2-(4-benzofuran-3-yl-piperidin-1-yl)-ethyl]-cyclohexylamine dihydrochloride (intermediate A) (100 mg, 0.25 mmol) and p-toluenesulfonyl chloride.

Example 39 trans-N-{4-[2-(4-Benzofuran-3-yl-piperidin-1-yl)-ethyl]-cyclohexyl}-2,2,2-trifluoro-acetamide

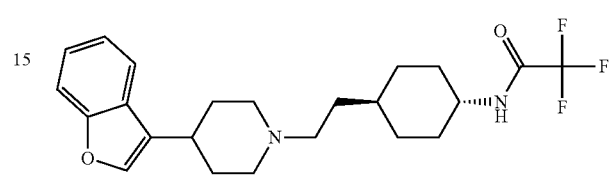

The title compound, off-white solid (41 mg, 39%), MS (ISP) m/z=423.2 [(M+H)$^+$], mp 152° C., was prepared in accordance with the general method of example 36 from trans-4-[2-(4-benzofuran-3-yl-piperidin-1-yl)-ethyl]-cyclohexylamine dihydrochloride (intermediate A) (100 mg, 0.25 mmol) and 2,2,2-trifluoroacetic acid anhydride.

Example 40 trans-N-{4-[2-(4-Benzofuran-3-yl-piperidin-1-yl)-ethyl]-cyclohexyl}-3,3-dimethyl-butyramide

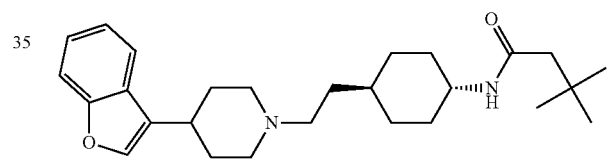

The title compound, off-white solid (83 mg, 78%), MS (ISP) m/z=425.3 [(M+H)$^+$], mp 174° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 3,3-dimethyl-butyric acid.

Example 41

3-Methyl-isoxazole-5-carboxylic acid trans-{4-[2-(4-benzofuran-3-yl-piperidin-1-yl)-ethyl]-cyclohexyl}-amide

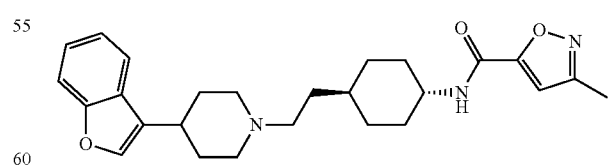

The title compound, off-white solid (89 mg, 82%), MS (ISP) m/z=436.3 [(M+H)$^+$], mp 178° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 3-methyl-isoxazole-5-carboxylic acid.

Example 42 trans-N-{4-[2-(4-Benzofuran-3-yl-piperidin-1-yl)-ethyl]-cyclohexyl}-N',N'-dimethyl-succinamide

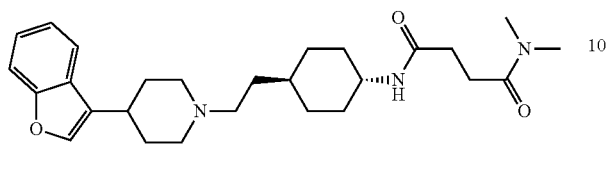

The title compound, off-white solid (55 mg, 48%), MS (ISP) m/z=454.4 [(M+H)⁺], mp 167° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-(dimethylamino)-4-oxobutanoic acid.

Example 43

N'-(trans-4-{2-[4-(benzofuran-3-yl)-piperidin-1-yl]-ethyl}-cyclohexyl)-N,N-dimethylsulfamide

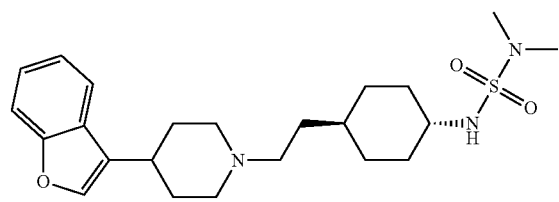 [SMILES: CN(C)S(=O)(=O)N[C@H]1CC[C@H](CCN2CCC(c3coc4ccccc34)CC2)CC1]

The title compound, light yellow solid (50 mg, 46%), MS (ISP) m/z=434.4 [(M+H)⁺], mp 229° C., was prepared in accordance with the general method of example 36 from trans-4-[2-(4-benzofuran-3-yl-piperidin-1-yl)-ethyl]-cyclohexylamine dihydrochloride (intermediate A) (100 mg, 0.25 mmol) and dimethylsulfamoyl chloride.

Example 44 trans-N-{4-[2-(4-Benzofuran-3-yl-piperidin-1-yl)-ethyl]-cyclohexyl}-4,4,4-trifluoro-butyramide

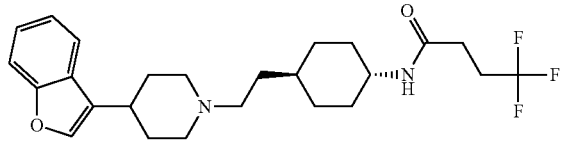 [SMILES: O=C(CCC(F)(F)F)N[C@H]1CC[C@H](CCN2CCC(c3coc4ccccc34)CC2)CC1]

The title compound, light brown solid (80 mg, 71%), MS (ISP) m/z=451.2 [(M+H)⁺], mp 192° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4,4,4-trifluoro-butanoic acid.

Example 45

4-Methyl-pentanoic acid trans-{4-[2-(4-benzofuran-3-yl-piperidin-1-yl)-ethyl]-cyclohexyl}-amide

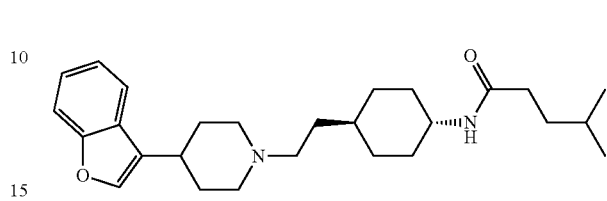

The title compound, off-white solid (72 mg, 68%), MS (ISP) m/z=425.3 [(M+H)⁺], mp 179° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-methyl-pentanoic acid.

Example 46

(R)-3-Hydroxy-pentanoic acid trans-{4-[2-(4-benzofuran-3-yl-piperidin-1-yl)-ethyl]-cyclohexyl}-amide

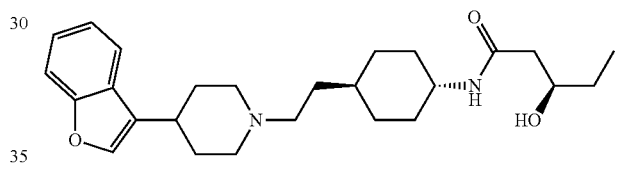

To a stirred solution of (R)-methyl 3-hydroxypentanoate (49.6 mg, 48.2 μl) in dioxane (3 ml) was added at room temperature potassium trimethylsilanolate (64.2 mg, 0 5 mmol) and the mixture was allowed to stir for additional 18 h. Afterwards N,N-diisopropylethylamine (178 mg, 1.38 mmol), trans-4-[2-(4-benzofuran-3-yl-piperidin-1-yl)-ethyl]-cyclohexylamine dihydrochloride (intermediate A) (100 mg, 0.25 mmol) and TBTU (121 mg, 0.376 mmol) were added, and the mixture was allowed to stir for 3 h at room temperature. The reaction mixture was poured into saturated NaHCO3 solution (20 ml) and extracted with dichloromethane (2×40 ml). The combined organic layers were washed with brine (20 ml), dried (MgSO4) and evaporated. The crude material (130 mg) was further purified by flash chromatography on silica gel (dichloromethane/MeOH/NH4OH 150:10:1) to yield the title compound as white solid (95 mg, 89%), MS (ISP) m/z=427.3 [(M+H)⁺], mp 142° C.

Example 47

(S)-3-Hydroxy-pentanoic acid trans-{4-[2-(4-benzofuran-3-yl-piperidin-1-yl)-ethyl]-cyclohexyl}-amide

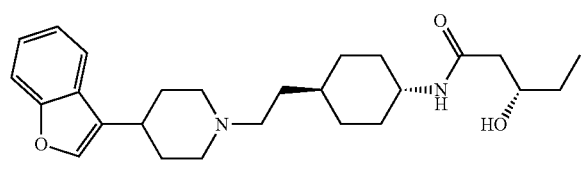 [SMILES: CC[C@H](O)CC(=O)N[C@H]1CC[C@H](CCN2CCC(c3coc4ccccc34)CC2)CC1]

The title compound, white solid (99 mg, 93%), MS (ISP) m/z=427.3 [(M+H)+], mp 140° C., was prepared in accordance with the general method of example 46 from trans-4-[2-(4-benzofuran-3-yl-piperidin-1-yl)-ethyl]-cyclohexylamine dihydrochloride (intermediate A) (100 mg, 0.25 mmol) and (S)-methyl 3-hydroxypentanoate.

Example 48 trans-N-{4-[2-(4-Benzofuran-3-yl-piperidin-1-yl)-ethyl]-cyclohexyl}-2-cyclobutyl-acetamide

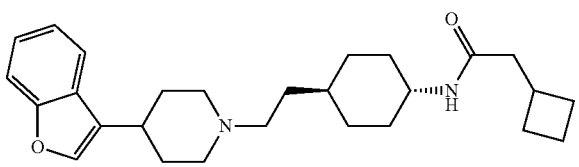

The title compound, off-white solid (68 mg, 64%), MS (ISP) m/z=423.3 [(M+H)+], mp 173° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-cyclobutyl-acetamide.

Example 49 trans-N-{4-[2-(4-Benzofuran-3-yl-piperidin-1-yl)-ethyl]-cyclohexyl}-4-chloro-benzamide

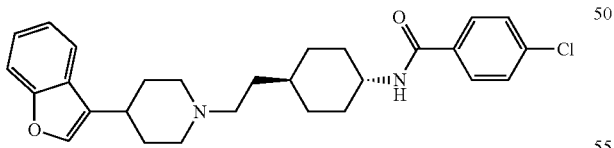

The title compound, light brown solid (95 mg, 82%), MS (ISP) m/z=465.2 [(M+H)+], mp 203° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-chloro-benzoic acid.

Example 50 trans-N-{4-[2-(4-Benzofuran-3-yl-piperidin-1-yl)-ethyl]-cyclohexyl}-4-trifluoromethyl-benzamide

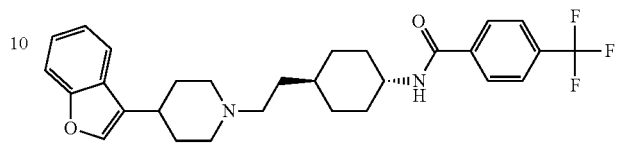

The title compound, light brown solid (98 mg, 78%), MS (ISP) m/z=499.4 [(M+H)+], mp 218° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-trifluoromethyl-benzoic acid.

Example 51 trans-N-{4-[2-(4-Benzofuran-3-yl-piperidin-1-yl)-ethyl]-cyclohexyl}-4-piperidin-1-yl-benzamide

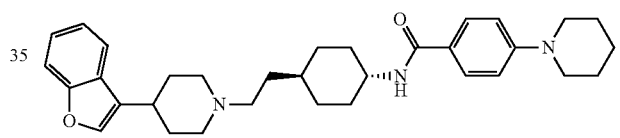

The title compound, off-white solid (95 mg, 72%), MS (ISP) m/z=514.4 [(M+H)+], mp 221° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-piperidin-1-yl-benzoic acid.

Example 52 trans-N-{4-[2-(4-Benzofuran-3-yl-piperidin-1-yl)-ethyl]-cyclohexyl}-3,3-dimethoxy-propionamide

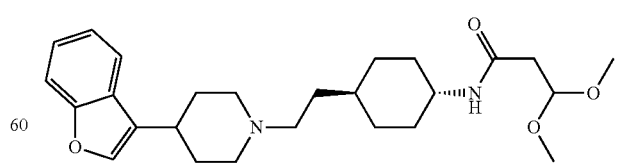

The title compound, white solid (71 mg, 64%), MS (ISP) m/z=443.4 [(M+H)+], mp 148° C., was prepared in accordance with the general method of example 46 from trans-4-[2-(4-benzofuran-3-yl-piperidin-1-yl)-ethyl]-cyclohexylamine dihydrochloride (intermediate A) (100 mg, 0.25 mmol) and methyl 3,3-dimethoxy-propanoate.

Example 53

3-Methyl-but-2-enoic acid trans-{4-[2-(4-benzofuran-3-yl-piperidin-1-yl)-ethyl]-cyclohexyl}-amide

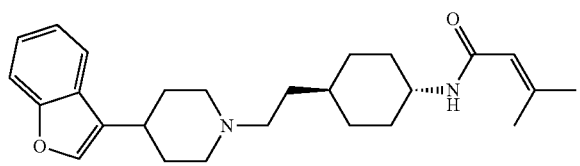 [SMILES: CC(C)=CC(=O)N[C@H]1CC[C@H](CCN2CCC(c3coc4ccccc34)CC2)CC1]

The title compound, off-white solid (83 mg, 81%), MS (ISP) m/z=409.4 [(M+H)⁺], mp 147° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 3-methyl-but-2-enoic acid.

Example 54

(E)-Pent-3-enoic acid trans-{4-[2-(4-benzofuran-3-yl-piperidin-1-yl)-ethyl]-cyclohexyl}-amide

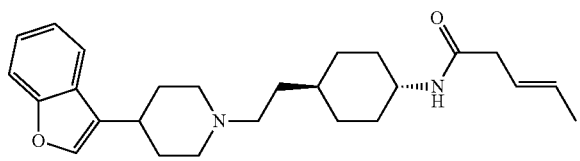 [SMILES: C/C=C/CC(=O)N[C@H]1CC[C@H](CCN2CCC(c3coc4ccccc34)CC2)CC1]

The title compound, white solid (71 mg, 70%), MS (ISP) m/z=409.4 [(M+H)⁺], mp 165° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and (E)-pent-3-enoic acid.

Example 55

But-2-ynoic acid trans-{4-[2-(4-benzofuran-3-yl-piperidin-1-yl)-ethyl]-cyclohexyl}-amide

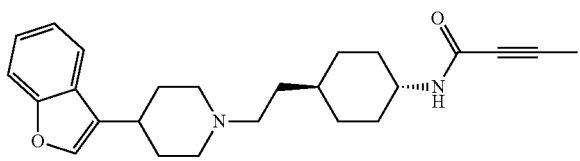 [SMILES: CC#CC(=O)N[C@H]1CC[C@H](CCN2CCC(c3coc4ccccc34)CC2)CC1]

The title compound, light brown solid (71 mg, 72%), MS (ISP) m/z=393.3 [(M+H)⁺], mp 161° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and but-2-ynoic acid.

Example 56 trans-N-{4-[2-(4-Benzofuran-3-yl-piperidin-1-yl)-ethyl]-cyclohexyl}-formamide

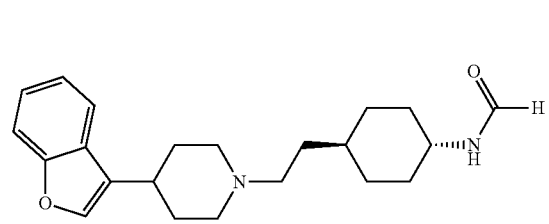 [SMILES: O=CN[C@H]1CC[C@H](CCN2CCC(c3coc4ccccc34)CC2)CC1]

The title compound, off-white solid (20 mg, 23%), MS (ISP) m/z=355.2 [(M+H)⁺], mp 155° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and formic acid.

Example 57

Pentanoic acid trans-{4-[2-(4-benzofuran-3-yl-piperidin-1-yl)-ethyl]-cyclohexyl}-amide

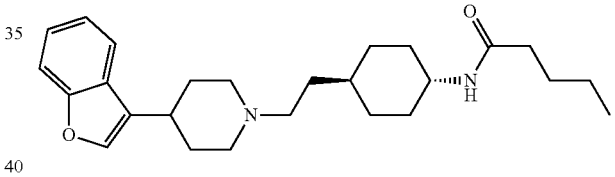

The title compound, off-white solid (77 mg, 75%), MS (ISP) m/z=411.5 [(M+H)⁺], mp 167° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and pentanoic acid.

Example 58

Benzo[1,3]dioxole-5-carboxylic acid trans-{4-[2-(4-benzofuran-3-yl-piperidin-1-yl)-ethyl]-cyclohexyl}-amide

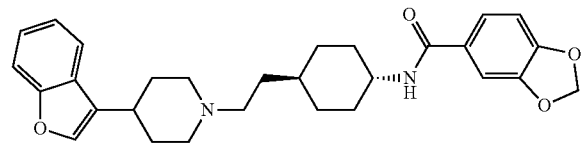 [SMILES: O=C(N[C@H]1CC[C@H](CCN2CCC(c3coc4ccccc34)CC2)CC1)c1ccc2c(c1)OCO2]

The title compound, off-white solid (97 mg, 82%), MS (ISP) m/z=475.3 [(M+H)⁺], mp 198° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and benzo[1,3]dioxole-5-carboxylic acid.

Example 59 trans-N-[4-{2-(4-Benzofuran-3-yl-piperidin-1-yl)-ethyl]-cyclohexyl}-4-pyrazol-1-yl-benzamide

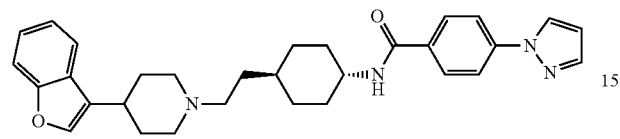

The title compound, light yellow solid (93 mg, 75%), MS (ISP) m/z=497.4 [(M+H)$^+$], mp 205° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-pyrazol-1-yl-benzoic acid.

Example 60 trans-N-{4-[2-(4-Benzofuran-3-yl-piperidin-1-yl)-ethyl]-cyclohexyl}-4-tert-butyl-benzamide

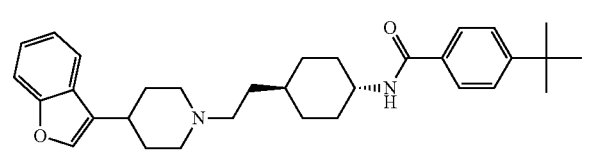 [SMILES: CC(C)(C)c1ccc(C(=O)N[C@H]2CC[C@H](CCN3CCC(c4coc5ccccc45)CC3)CC2)cc1]

The title compound, yellow solid (110 mg, 90%), MS (ISP) m/z=487.5 [(M+H)$^+$], mp 180° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-tert-butyl-benzoic acid.

Example 61 trans-N-{4-[2-(4-Benzofuran-3-yl-piperidin-1-yl)-ethyl]-cyclohexyl}-4-(5-methyl-[1,2,4]oxadiazol-3-yl)-benzamide

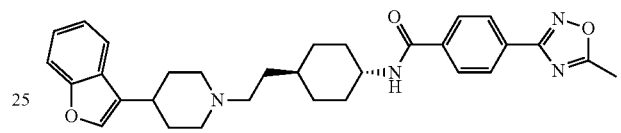

The title compound, yellow solid (111 mg, 87%), MS (ISP) m/z=513.3 [(M+H)$^+$], mp 194° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-(5-methyl-[1,2,4]oxadiazol-3-yl)-benzoic acid.

Example 62 trans-N-{4-[2-(4-Benzofuran-3-yl-piperidin-1-yl)-ethyl]-cyclohexyl}-4-(4-methyl-piperazin-1-yl)-benzamide

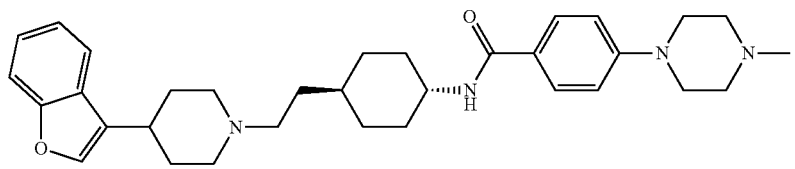 [SMILES: CN1CCN(c2ccc(C(=O)N[C@H]3CC[C@H](CCN4CCC(c5coc6ccccc56)CC4)CC3)cc2)CC1]

The title compound, off-white solid (56 mg, 42%), MS (ISP) m/z=529.4 [(M+H)+], mp 242° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-(4-methyl-piperazin-1-yl)-benzoic acid.

Example 63

Biphenyl-4-carboxylic acid trans-{4-[2-(4-benzofuran-3-yl-piperidin-1-yl)-ethyl]-cyclohexyl}-amide

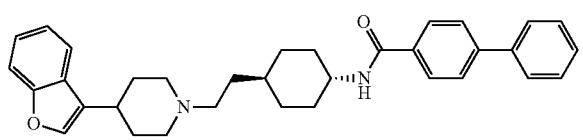 [SMILES: O=C(N[C@H]1CC[C@H](CCN2CCC(c3coc4ccccc34)CC2)CC1)c1ccc(-c2ccccc2)cc1]

The title compound, yellow solid (119 mg, 94%), MS (ISP) m/z=507.3 [(M+H)+], mp 235° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and biphenyl-4-carboxylic acid.

Example 64 trans-N-{4-[2-(4-Benzofuran-3-yl-piperidin-1-yl)-ethyl]-cyclohexyl}-4-pyridin-3-yl-benzamide

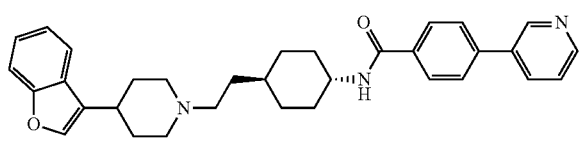

The title compound, off-white solid (98 mg, 77%), MS (ISP) m/z=508.4 [(M+H)+], mp 224° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-pyridin-3-yl-benzoic acid.

Example 65 trans-N-{4-[2-(4-Benzofuran-3-yl-piperidin-1-yl)-ethyl]-cyclohexyl}-6-morpholin-4-yl-nicotinamide

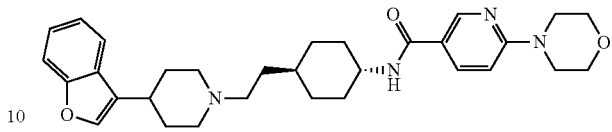

The title compound, light yellow solid (81 mg, 63%), MS (ISP) m/z=517.3 [(M+H)+], mp 215° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 6-morpholin-4-yl-nicotinic acid.

Example 66 trans-N-{4-[2-(4-Benzofuran-3-yl-piperidin-1-yl)-ethyl]-cyclohexyl}-4-(1,1-dioxo-1λ6-thiomorpholin-4-yl)-benzamide

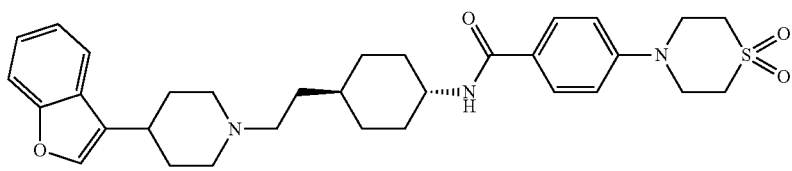 [SMILES: O=C(N[C@H]1CC[C@H](CCN2CCC(c3coc4ccccc34)CC2)CC1)c1ccc(N2CCS(=O)(=O)CC2)cc1]

The title compound, light yellow solid (116 mg, 82%), MS (ISP) m/z=564.4 [(M+H)+], mp 269° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-(1,1-dioxo-1λ6-thiomor-pholin-4-yl)-benzoic acid.

Example 67

5-Morpholin-4-yl-pyrazine-2-carboxylic acid trans-{4-[2-(4-benzofuran-3-yl-piperidin-1-yl)-ethyl]-cyclohexyl}-amide

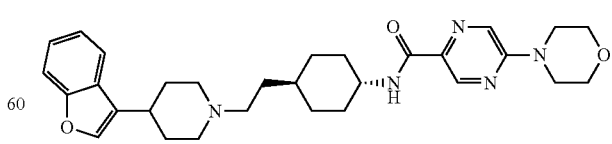

The title compound, off-white solid (95 mg, 73%), MS (ISP) m/z=518.4 [(M+H)+], mp 202° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 5-morpholin-4-yl-pyrazine-2-carboxylic acid.

Example 68 trans-N-{4-[2-(4-Benzofuran-3-yl-piperidin-1-yl)-ethyl]-cyclohexyl}-4-pyrrol-1-yl-benzamide

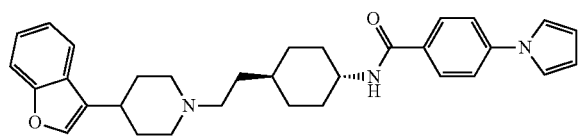

The title compound, off-white solid (77 mg, 62%), MS (ISP) m/z=496.4 [(M+H)⁺], mp 212° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-pyrrol-1-yl-benzoic acid.

Example 69 trans-N-{4-[2-(4-Benzofuran-3-yl-piperidin-1-yl)-ethyl]-cyclohexyl}-6-methyl-nicotinamide

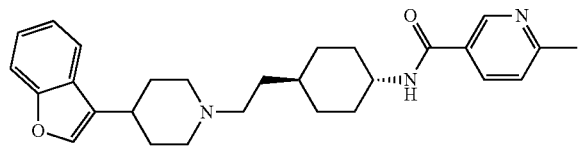 [SMILES: Cc1ccc(C(=O)N[C@H]2CC[C@H](CCN3CCC(c4coc5ccccc45)CC3)CC2)cn1]

The title compound, yellow solid (66 mg, 59%), MS (ISP) m/z=446.4 [(M+H)⁺], mp 203° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 6-methyl-nicotinic acid.

Example 70 trans-N-{4-[2-(4-Benzofuran-3-yl-piperidin-1-yl)-ethyl]-cyclohexyl}-4-cyano-benzamide

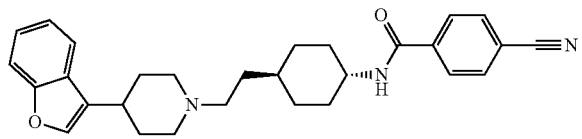 [SMILES: N#Cc1ccc(C(=O)N[C@H]2CC[C@H](CCN3CCC(c4coc5ccccc45)CC3)CC2)cc1]

The title compound, yellow solid (54 mg, 47%), MS (ISP) m/z=456.5 [(M+H)⁺], mp 195° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-cyano-benzoic acid.

Example 71 trans-N-{4-[2-(4-Benzofuran-3-yl-piperidin-1-yl)-ethyl]-cyclohexyl}-4-tert-butoxy-benzamide

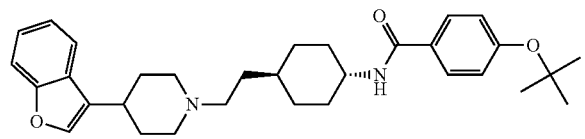 [SMILES: CC(C)(C)Oc1ccc(C(=O)N[C@H]2CC[C@H](CCN3CCC(c4coc5ccccc45)CC3)CC2)cc1]

The title compound, white solid (82 mg, 65%), MS (ISP) m/z=503.3 [(M+H)⁺], mp 186° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-tert-butoxy-benzoic acid.

Example 72 trans-N-{4-[2-(4-Benzofuran-3-yl-piperidin-1-yl)-ethyl]-cyclohexyl}-2-trans-(4-methoxy-cyclohexyl)-acetamide

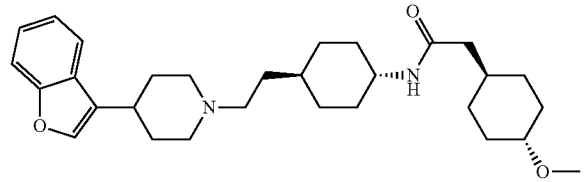 [SMILES: CO[C@H]1CC[C@H](CC(=O)N[C@H]2CC[C@H](CCN3CCC(c4coc5ccccc45)CC3)CC2)CC1]

The title compound, off-white solid (70 mg, 58%), MS (ISP) m/z=481.4 [(M+H)⁺], mp 179° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and trans-(4-methoxy-cyclohexyl)-acetic acid.

Example 73

Quinoline-6-carboxylic acid trans-{4-[2-(4-benzofuran-3-yl-piperidin-1-yl)-ethyl]-cyclohexyl}-amide

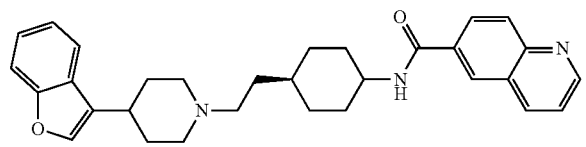

The title compound, yellow solid (106 mg, 88%), MS (ISP) m/z=482.4 [(M+H)⁺], mp 192° C., was prepared in accordance with the general method of example 1 from trans-4-[2-

(4-benzofuran-3-yl-piperidin-1-yl)-ethyl]-cyclohexylamine dihydrochloride (intermediate A) (100 mg, 0.25 mmol) and quinoline-6-carboxylic acid.

Example 74 trans-2-Benzo[1,3]dioxol-5-yl-N-{4-[2-(4-benzofuran-3-yl-piperidin-1-yl)-ethyl]-cyclohexyl}-acetamide

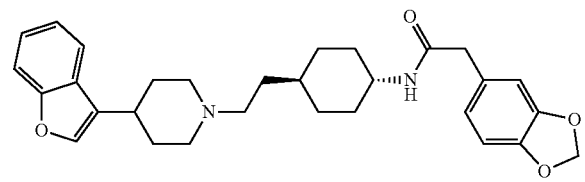 [SMILES: O=C(Cc1ccc2c(c1)OCO2)N[C@H]1CC[C@H](CCN2CCC(c3coc4ccccc34)CC2)CC1]

The title compound, off-white solid (79 mg, 65%), MS (ISP) m/z=489.3 [(M+H)+], mp 177° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-(benzo[1,3]dioxol-5-yl)-acetic acid.

Example 75

5-Methanesulfonyl-thiophene-2-carboxylic acid trans-{4-[2-(4-benzofuran-3-yl-piperidin-1-yl)-ethyl]-cyclohexyl}-amide

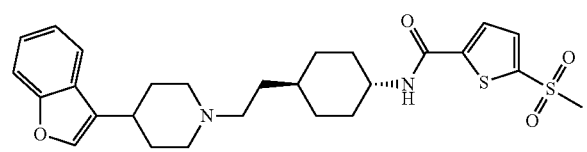 [SMILES: CS(=O)(=O)c1ccc(C(=O)N[C@H]2CC[C@H](CCN3CCC(c4coc5ccccc45)CC3)CC2)s1]

The title compound, yellow solid (101 mg, 78%), MS (ISP) m/z=515.3 [(M+H)+], mp 214° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 5-methanesulfonyl-thiophene-2-carboxylic acid.

Example 76 trans-N-{4-[2-(4-Benzofuran-3-yl-piperidin-1-yl)-ethyl]-cyclohexyl}-2-oxetan-3-yl-acetamide

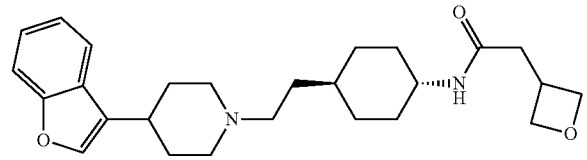

The title compound, white solid (99 mg, 93%), MS (ISP) m/z=425.4 [(M+H)+], mp 197° C., was prepared in accordance with the general method of example 46 from trans-4-[2-(4-benzofuran-3-yl-piperidin-1-yl)-ethyl]-cyclohexylamine dihydrochloride (intermediate A) (100 mg, 0.25 mmol) and methyl 2-(oxetan-3-yl) acetate.

Example 77

4-tert-Butyl-cyclohexanecarboxylic acid trans-{4-[2-(4-benzofuran-3-yl-piperidin-1-yl)-ethyl]-cyclohexyl}-amide

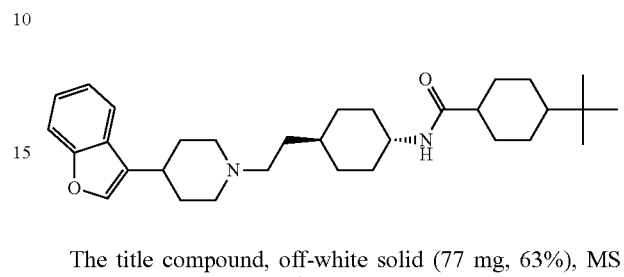

The title compound, off-white solid (77 mg, 63%), MS (ISP) m/z=493.4 [(M+H)+], mp 199° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-tert-butyl-cyclohexanecarboxylic acid.

Example 78

Adamantane-1-carboxylic acid trans-{4-[2-(4-benzofuran-3-yl-piperidin-1-yl)-ethyl]-cyclohexyl}-amide

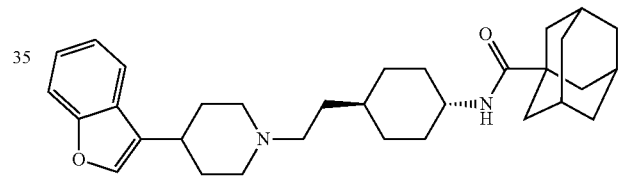

The title compound, light yellow solid (94 mg, 77%), MS (ISP) m/z=489.4 [(M+H)+], mp 200° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and adamantane-1-carboxylic acid.

Example 79

4-Trifluoromethyl-cyclohexanecarboxylic acid trans-{4-[2-(4-benzofuran-3-yl-piperidin-1-yl)-ethyl]-cyclohexyl}-amide

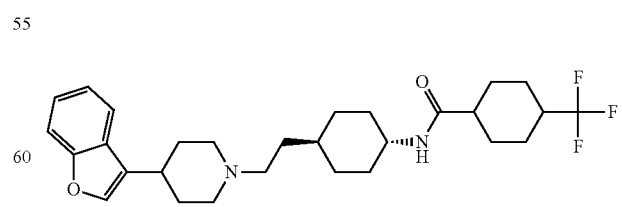

The title compound, white solid (42 mg, 33%), MS (ISP) m/z=505.3 [(M+H)+], mp 190° C., was prepared in accordance with the general method of example 1 from trans-4-[2-(4-benzofuran-3-yl-piperidin-1-yl)-ethyl]-cyclohexylamine

Example 80 trans-N-{4-[2-(4-Benzofuran-3-yl-piperidin-1-yl)-ethyl]-cyclohexyl}-4-isobutyl-benzamide

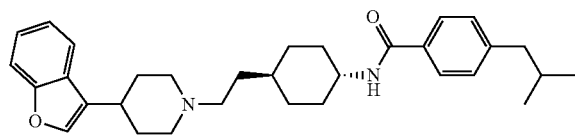 [SMILES: CC(C)Cc1ccc(C(=O)N[C@H]2CC[C@H](CCN3CCC(c4coc5ccccc45)CC3)CC2)cc1]

The title compound, off-white solid (89 mg, 73%), MS (ISP) m/z=487.4 [(M+H)$^+$], mp 190° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-isobutyl-benzoic acid.

Example 81 trans-N-{4-[2-(4-Benzofuran-3-yl-piperidin-1-yl)-ethyl]-cyclohexyl}-4-ethyl-benzamide

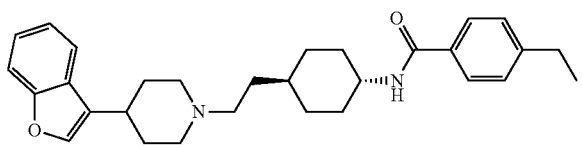 [SMILES: CCc1ccc(C(=O)N[C@H]2CC[C@H](CCN3CCC(c4coc5ccccc45)CC3)CC2)cc1]

The title compound, white solid (94 mg, 82%), MS (ISP) m/z=459.5 [(M+H)$^+$], mp 192° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-ethyl-benzoic acid.

Example 82 trans-N-{4-[2-(4-Benzofuran-3-yl-piperidin-1-yl)-ethyl]-cyclohexyl}-4-cyclohexyl-benzamide

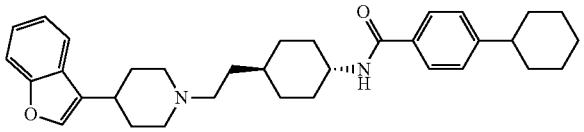 [SMILES: O=C(N[C@H]1CC[C@H](CCN2CCC(c3coc4ccccc34)CC2)CC1)c1ccc(C2CCCCC2)cc1]

The title compound, white solid (114 mg, 89%), MS (ISP) m/z=513.6 [(M+H)$^+$], mp 230° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-cyclohexyl-benzoic acid.

Example 83 trans-N-{4-[2-(4-Benzofuran-3-yl-piperidin-1-yl)-ethyl]-cyclohexyl}-4-isopropyl-benzamide

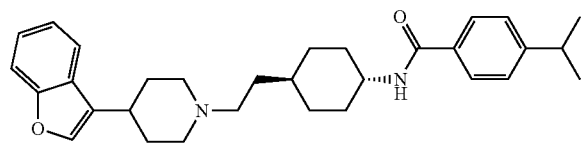 [SMILES: CC(C)c1ccc(C(=O)N[C@H]2CC[C@H](CCN3CCC(c4coc5ccccc45)CC3)CC2)cc1]

The title compound, light yellow solid (42 mg, 36%), MS (ISP) m/z=473.4 [(M+H)$^+$], mp 188° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-isopropyl-benzoic acid.

Example 84 trans-N-{4-[2-(4-Benzofuran-3-yl-piperidin-1-yl)-ethyl]-cyclohexyl}-4-cyclopropyl-benzamide

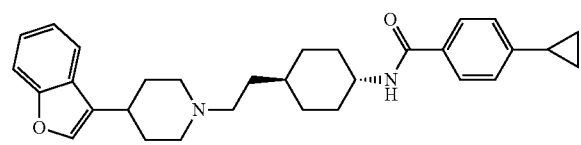 [SMILES: O=C(N[C@H]1CC[C@H](CCN2CCC(c3coc4ccccc34)CC2)CC1)c1ccc(C2CC2)cc1]

The title compound, light yellow solid (85 mg, 72%), MS (ISP) m/z=471.4 [(M+H)$^+$], mp 199° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-cyclopropyl-benzoic acid.

Example 85 trans-2-Benzo[d]isoxazol-3-yl-N-{4-[2-(4-benzofuran-3-yl-piperidin-1-yl)-ethyl]-cyclohexyl}-acetamide

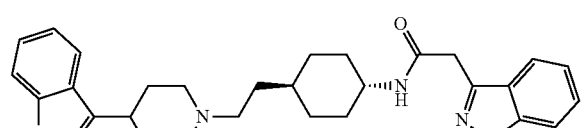

The title compound, white solid (93 mg, 76%), MS (ISP) m/z=486.4 [(M+H)$^+$], mp 175° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2-benzo[d]isoxazol-acetic acid.

Example 86 trans-N-{4-[2-(4-Benzofuran-3-yl-piperidin-1-yl)-ethyl]-cyclohexyl}-4-methanesulfonyl-benzamide

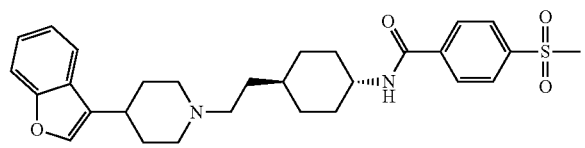 [SMILES: CS(=O)(=O)c1ccc(C(=O)N[C@H]2CC[C@H](CCN3CCC(c4coc5ccccc45)CC3)CC2)cc1]

The title compound, off-white solid (95 mg, 75%), MS (ISP) m/z=509.3 [(M+H)$^+$], mp 224° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 4-methanesulfonyl-benzoic acid.

Example 87 trans-N-{4-[2-(4-Benzofuran-3-yl-piperidin-1-yl)-ethyl]-cyclohexyl}-2,4-dichloro-benzamide

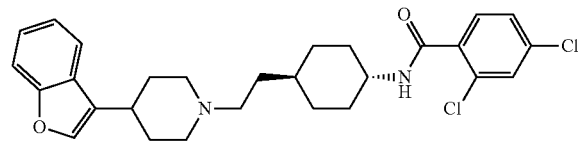

The title compound, light yellow solid (88 mg, 70%), MS (ISP) m/z=499.3 [(M+H)$^+$], mp 187° C., was prepared in accordance with the general method of example 1 from trans-4-[2-(4-benzofuran-3-yl-piperidin-1-yl)-ethyl]-cyclohexylamine dihydrochloride (intermediate A) (100 mg, 0.25 mmol) and 2,4-dichloro-benzoic acid.

Example 88 trans-N-{4-[2-(4-Benzofuran-3-yl-piperidin-1-yl)-ethyl]-cyclohexyl}-4-tert-butyl-benzenesulfonamide

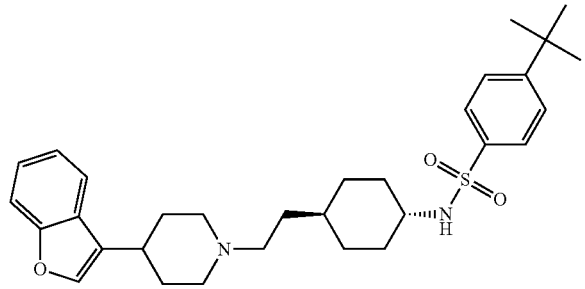 [SMILES: CC(C)(C)c1ccc(S(=O)(=O)N[C@H]2CC[C@H](CCN3CCC(c4coc5ccccc45)CC3)CC2)cc1]

The title compound, white solid (92 mg, 70%), MS (ISP) m/z=523.6 [(M+H)$^+$], mp 171° C., was prepared in accordance with the general method of example 36 from trans-4-[2-(4-benzofuran-3-yl-piperidin-1-yl)-ethyl]-cyclohexylamine dihydrochloride (intermediate A) (100 mg, 0.25 mmol) and 4-tert-butyl-benzenesulfonyl chloride.

Biochemical Assay

The ability of the compounds to bind to the 5-HT$_{2A}$, D$_3$ and D$_2$ receptors was determined using radioligand binding to cloned receptors selectively expressed in HEK-293 EBNA cells.

Membrane Preparation

HEK293 EBNA cells were transiently transfected with expression plasmids encoding for the human D$_2$ or D$_3$ or for the human 5-HT$_{2A}$ receptor, respectively. The cells were harvested 48 h post-transfection, washed three times with cold PBS and stored at −80° C. prior to use. The pellet was suspended in cold 50 mM Tris-HCl buffer containing 10 mM EDTA (pH 7.4) and was homogenized with a Polytron (Kinematica AG, Basel, Switzerland) for 20-30 sec at 12.000 rpm. After centrifugation at 48.000×g for 30 min at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay

Aliquots of membrane preparations were thawed at RT, resuspended in assay buffer (D$_2$, D$_3$: 50 mM Tris-HCl, 120 mM NaCl, 5 mM MgCl$_2$, 1 mM EDTA, 5 mM KCl, 1.5 mM CaCl$_2$, pH=7.4; 5-HT$_{2A}$: 50 mM Tris-HCl, 10 mM MgCl$_2$, 1 mM EGTA, pH=7.4), homogenized with a Polytron for 20-30 sec at 12.000 rpm and adjusted to a final concentration of approximately 7.5 µg protein/well (D$_2$, D$_3$) and 15 µg protein/well (5-HT$_{2A}$), respectively.

The binding affinity (K$_i$) of the compounds was determined using radioligand binding.

Membranes were incubated in a total volume of 200 µl with a fixed concentration of radioligand (final concentration approximately 0.7 nM [$^3$H]-spiperone for D$_2$, 0.5 nM [$^3$H]-spiperone for D$_3$, and 1.1 nM [$^3$H]-ketanserin for 5-HT$_{2A}$) and ten concentrations of test compound in ranging between 10 µM-0.1 nM for 1 h at RT. At the end of the incubation, the reaction mixtures were filtered on to unifilter 96-well white microplates with bonded GF/C filters (Packard BioScience, Zürich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 µM unlabelled spiperone. Per well 45 µl of Microscint 40 (Perkin Elmer, Schwerzenbach, Switzerland) was added, plates for sealed, shaken for 20 min and counted for 3 min on a Topcount Microplate Scintillation Counter (Canberra Packard SA, Zürich, Switzerland) with quenching correction.

Data Calculation

The CPM value for each duplicate of a concentration of competing compound was averaged (y1), then the % specific binding was calculated according to the equation (((y1−nonspecific)/(total binding−non-specific))×100). Graphs were plotted with the % specific binding using XLfit, a curvefitting program that iteratively plots the data using Levenberg-Marquardt algorithm. The single site competition analysis equation used was y=A+((B−A)/(1+((x/C)D))), where y is the % specific binding, A is the minimum y, B is the maximum y, C is the $IC_{50}$, x is the log 10 of the concentration of the competing compound and D is the slope of the curve (the Hill Coefficient). From these curves the $IC_{50}$ (inhibition concentration at which 50% specific binding of the radioligand was displaced) and Hill coefficient were determined. The affinity constant ($K_i$) was calculated using the Cheng-Prusoff equation $K_i=(IC_{50}/1+([L]/K_d)$, where [L] is the concentration of radioligand and $K_d$ is the dissociation constant of the radioligand at the receptor as determined by the saturation isotherm.

The compounds of the present invention are selective dual modulators of the $5-HT_{2A}$ and $D_3$ receptors as is shown in table 1 below. Examples were tested in the above assay and found to have $K_i$ $5-HT_{2A}$ values of about 0.1 nM to about 1 μM and $K_i$ $D_3$ values of about 0.1 nM to about 1 μM. Particular compounds of formula (I) were found to have $K_i$ $5-HT_{2A}$ values of about 0.1 nM to about 100 nM and $K_i$ $D_3$ values of about 0.1 nM to about 200 nM. More particular compounds of formula (I) were found to have $K_i$ $5-HT_{2A}$ values of about 1 nM to about 50 nM and $K_i$ $D_3$ values of about 0.1 nM to about 50 nM. More particular compounds of formula (I) were found to have $K_i$ $5-HT_{2A}$ values of about 1 nM to about 10 nM and $K_i$ $D_3$ values of about 0.1 nM to about 10 nM.

Particular compounds of formula (I) were found to bind more selectively to the $5-HT_{2A}$ receptor than to the $D_2$ receptor by a factor of 5 or more, more particularly 10 or more, most particularly 15 or more. Particular compounds of formula (I) were found to bind more selectively to the $D_3$ receptor than to the $D_2$ receptor by a factor of 5 or more, more particularly 10 or more, most particularly 15 or more.

A particular embodiment of the present invention provides compounds of formula (I) or pharmaceutically acceptable salts and esters thereof which bind more selectively to the $5-HT_{2A}$ receptor than to the $D_2$ receptor by a factor of 14 or more and which bind more selectively to the $D_3$ receptor than to the $D_2$ receptor by a factor of 15 or more.

TABLE 1

Binding affinities to HEK293 EBNA cells expressing human (h) receptors of representative examples.

| Ex. | $D_2$ Ki [nM] | $D_3$ Ki [nM] | $5-HT_{2A}$ Ki [nM] |
|---|---|---|---|
| 1 | 50.40 | 1.08 | 5.08 |
| 2 | 71.18 | 1.22 | 4.63 |
| 3 | 37.32 | 4.53 | 2.44 |
| 4 | 77.56 | 3.14 | 5.37 |
| 5 | 48.10 | 1.23 | 4.52 |
| 6 | 80.10 | 3.52 | 3.36 |
| 7 | 50.80 | 1.45 | 3.54 |
| 8 | 85.90 | 2.02 | 2.04 |
| 9 | 32.32 | 1.34 | 4.36 |
| 10 | 83.59 | 0.68 | 7.71 |
| 11 | 46.52 | 1.47 | 4.92 |
| 12 | 42.66 | 0.99 | 8.06 |
| 13 | 406.32 | 7.40 | 11.08 |
| 14 | 39.54 | 1.78 | 5.75 |
| 15 | 43.49 | 1.94 | 8.65 |
| 16 | 53.71 | 5.51 | 2.25 |
| 17 | 52.97 | 2.22 | 5.93 |
| 18 | 81.48 | 9.20 | 2.88 |
| 19 | 96.68 | 3.36 | 8.70 |
| 20 | 38.05 | 1.85 | 5.56 |
| 21 | 62.94 | 1.27 | 8.26 |
| 22 | 47.49 | 1.48 | 3.05 |
| 23 | 41.51 | 0.84 | 5.96 |
| 24 | 68.89 | 3.05 | 5.66 |
| 25 | 33.71 | 2.24 | 5.16 |
| 26 | 37.09 | 5.88 | 4.70 |
| 27 | 22.68 | 2.69 | 4.30 |
| 28 | 37.96 | 12.74 | 6.05 |
| 29 | 52.86 | 2.75 | 5.43 |
| 30 | 28.11 | 3.53 | 8.59 |
| 31 | 46.02 | 4.83 | 6.56 |
| 32 | 46.39 | 4.02 | 6.08 |
| 33 | 45.27 | 1.71 | 5.53 |
| 34 | 41.33 | 2.25 | 5.10 |
| 35 | 50.42 | 2.29 | 9.69 |
| 36 | 47.35 | 2.85 | 5.43 |
| 37 | 47.99 | 2.87 | 5.07 |
| 38 | 58.62 | 6.24 | 41.46 |
| 39 | 37.47 | 4.08 | 8.62 |
| 40 | 53.03 | 4.35 | 10.36 |
| 41 | 36.41 | 4.23 | 9.21 |
| 42 | 92.30 | 2.43 | 7.80 |
| 43 | 47.02 | 3.02 | 4.41 |
| 44 | 61.16 | 2.94 | 14.96 |
| 45 | 65.98 | 2.90 | 13.06 |
| 46 | 55.43 | 2.49 | 8.70 |
| 47 | 33.75 | 2.25 | 9.10 |
| 48 | 58.22 | 2.05 | 4.94 |
| 49 | 25.80 | 3.22 | 9.01 |
| 50 | 151.81 | 2.21 | 4.75 |
| 51 | 345.18 | 4.39 | 6.85 |
| 52 | 48.85 | 1.46 | 5.94 |
| 53 | 18.01 | 2.83 | 9.68 |
| 54 | 57.95 | 1.81 | 12.26 |
| 55 | 25.62 | 2.09 | 7.89 |
| 56 | 38.76 | 2.68 | 13.40 |
| 57 | 65.71 | 2.21 | 13.04 |
| 58 | 28.63 | 2.79 | 8.78 |
| 59 | 46.90 | 5.73 | 22.18 |
| 60 | 1111.22 | 10.07 | 3.77 |
| 61 | 226.91 | 2.87 | 15.11 |
| 62 | 50.09 | 6.03 | 8.83 |
| 63 | 22.11 | 3.37 | 5.21 |
| 64 | 16.72 | 4.55 | 12.76 |
| 65 | 51.80 | 3.49 | 7.56 |
| 66 | 19.22 | 3.40 | 10.07 |
| 67 | 105.59 | 7.72 | 8.20 |
| 68 | 34.26 | 4.58 | 10.17 |
| 69 | 28.13 | 2.53 | 5.11 |
| 70 | 15.19 | 2.68 | 5.89 |
| 71 | 168.26 | 2.14 | 5.56 |
| 72 | 67.41 | 3.09 | 8.14 |
| 73 | 102.85 | 2.42 | 11.01 |
| 74 | 92.47 | 1.66 | 11.50 |
| 75 | 60.84 | 3.89 | 7.85 |
| 76 | 34.19 | 1.64 | 5.25 |
| 77 | 344.55 | 9.48 | 6.03 |
| 78 | 129.19 | 12.72 | 17.38 |
| 79 | 72.97 | 6.80 | 11.18 |
| 80 | 291.61 | 4.16 | 2.69 |
| 81 | 204.42 | 1.33 | 2.53 |
| 82 | inact. | 41.33 | 5.81 |
| 83 | 401.84 | 4.80 | 2.60 |
| 84 | 355.25 | 14.08 | 2.15 |
| 85 | 244.83 | 145.21 | 8.22 |

TABLE 1-continued

Binding affinities to HEK293 EBNA cells expressing human (h) receptors of representative examples.

| Ex. | D$_2$ Ki [nM] | D$_3$ Ki [nM] | 5-HT$_{2A}$ Ki [nM] |
|---|---|---|---|
| 86 | 79.51 | 25.04 | 5.79 |
| 87 | 38.17 | 4.37 | 12.26 |
| 88 | 70.03 | 12.13 | 31.52 |

The invention claimed is:
1. A compound of formula (I)

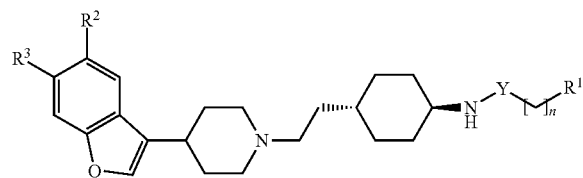

(I)

wherein
n is 0, 1, 2, 3 or 4;
Y is —C(O)— or —S(O)$_2$—;
R$^1$ is hydrogen, alkyl, alkenyl, alkynyl, haloalkyl, cycloalkyl, adamantyl, heterocycloalkyl, aryl, aryl anellated to heterocycloalkyl, heteroaryl, —NR$^6$R$^7$, hydroxy, alkoxy, or haloalkoxy;
wherein alkyl, alkenyl, alkynyl, haloalkyl, alkoxy and haloalkoxy are each optionally substituted by one, two or three independent R$^4$; and
wherein cycloalkyl, adamantyl, heterocycloalkyl, aryl, aryl anellated to heterocycloalkyl, and heteroaryl are each optionally substituted by one, two or three independent R$^5$;
R$^2$ and R$^3$ are each hydrogen;
R$^4$ is cyano, cycloalkyl, heterocycloalkyl, aryl, heteroaryl, —C(O)NR$^6$R$^7$, —NR$^6$R$^7$, —NH(CO)-alkyl, hydroxy, alkoxy, haloalkoxy, oxo, or —S(O)$_2$R$^6$;
wherein cycloalkyl, heterocycloalkyl, aryl, and heteroaryl, are each optionally substituted by one, two or three independent R$^5$;
R$^5$ is halogen, cyano, alkyl, haloalkyl, cycloalkyl, heterocycloalkyl, aryl, heteroaryl, —C(O)NR$^6$R$^7$, —NR$^6$R$^7$, —NH(CO)-alkyl, hydroxy, alkoxy, haloalkoxy, oxo, or —S(O)$_2$R$^6$;
wherein cycloalkyl, heterocycloalkyl, aryl, and heteroaryl, are each optionally substituted by one, two or three substituents independently selected from halogen, cyano, alkyl, haloalkyl, hydroxy, alkoxy, haloalkoxy, and oxo;
R$^6$ and R$^7$ are each independently hydrogen, alkyl, haloalkyl, cycloalkyl, cycloalkylalkyl, heterocycloalkyl, heterocycloalkylalkyl, aryl, or heteroaryl;
or a pharmaceutically acceptable salt or ester thereof.
2. The compound of claim 1, wherein n is 0, 1 or 2.
3. The compound of claim 1, wherein Y is —C(O)—.
4. The compound of claim 1, wherein R$^1$ is hydrogen, alkyl, alkenyl, alkynyl, haloalkyl, cycloalkyl, adamantyl, heterocycloalkyl, aryl, aryl anellated to heterocycloalkyl, heteroaryl, —NR$^6$R$^7$, hydroxy, alkoxy, or haloalkoxy; wherein alkyl, and haloalkyl, are each optionally substituted by one, two or three independent R$^4$; and wherein cycloalkyl, aryl, and heteroaryl are each optionally substituted by one, two or three independent R$^5$.
5. The compound of claim 4, wherein R$^1$ is hydrogen, methyl, methyl substituted by methoxy, n-propyl, n-propyl substituted by hydroxy, iso-propyl, iso-propyl substituted by hydroxy, n-butyl, tert-butyl, n-propenyl, iso-butenyl, propynyl, trifluoromethyl, trifluoroethyl, trifluoroethyl substituted by hydroxy, cyclopropyl, cyclopropyl substituted by fluoro, cyclopropyl substituted by hydroxy, cyclobutyl, cyclohexyl, cyclohexyl substituted by tert-butyl, cyclohexyl substituted by trifluoromethyl, cyclohexyl substituted by methoxy, adamantyl, oxetanyl, tetrahydrofuranyl, tetrahydropyranyl, dioxanyl, phenyl, phenyl substituted by R$^8$, benzodioxolyl, isoxazolyl, isoxazolyl substituted by methyl, thienyl, thienyl substituted by methyl-sulfonyl, pyridinyl, pyridinyl substituted by methyl, pyridinyl substituted by morpholinyl, pyrazinyl, pyrazinyl substituted by morpholinyl, quinolinyl, benzoisoxazolyl, —N(methyl)$_2$, hydroxy, or methoxy;
and wherein R$^8$ is selected from fluoro, chloro, cyano, methyl, ethyl, iso-propyl, iso-butyl, tert-butyl, trifluoromethyl, cyclopropyl, cyclohexyl, piperidinyl, methyl-piperazinyl, morpholinyl, dioxo-thiomorpholinyl, phenyl, pyrrolyl, pyrazolyl, methyl-oxadiazolyl, pyridinyl, tert-butoxy, and methyl-sulfonyl.
6. The compound of claim 5, wherein R$^1$ is cyclohexyl, cyclohexyl substituted by tert-butyl, tetrahydropyranyl, dioxanyl, methoxy, phenyl, or phenyl substituted by a substituent selected from the group consisting of ethyl, iso-propyl, iso-butyl, tert-butyl, trifluoromethyl, cyclopropyl, piperidinyl, morpholinyl, methyl-oxadiazolyl, and tert-butoxy.
7. The compound of claim 1, wherein R$^4$ is cyano, —C(O)—NR$^6$R$^7$, hydroxy, alkoxy, or —S(O)$_2$R$^6$.
8. The compound of claim 7, wherein R$^4$ is cyano, —C(O)N(methyl)$_2$, hydroxy, methoxy, or methyl-sulfonyl.
9. The compound of claim 1, wherein R$^5$ is halogen, cyano, alkyl, haloalkyl, cycloalkyl, heterocycloalkyl, aryl, heteroaryl, hydroxy, alkoxy, or alkylsulfonyl; wherein heterocycloalkyl, and heteroaryl are each optionally substituted by one, two or three substituents independently selected from alkyl, and oxo.
10. The compound of claim 9, wherein R$^5$ is fluoro, chloro, cyano, methyl, ethyl, iso-propyl, iso-butyl, tert-butyl, trifluoromethyl, cyclopropyl, cyclohexyl, piperidinyl, methyl-piperazinyl, morpholinyl, dioxo-thiomorpholinyl, phenyl, pyrrolyl, pyrazolyl, methyl-oxadiazolyl, pyridinyl, hydroxy, methoxy, tert-butoxy, or methyl-sulfonyl.
11. The compound of claim 10, wherein R$^5$ is ethyl, iso-propyl, iso-butyl, tert-butyl, trifluoromethyl, cyclopropyl, piperidinyl, morpholinyl, methyl-oxadiazolyl, or tert-butoxy.
12. The compound of claim 1, wherein R$^6$ and R$^7$ are each independently selected from alkyl.
13. The compound of claim 12, wherein R$^6$ and R$^7$ are each methyl.
14. The compound of claim 1, selected from the group consisting of:
trans-N-{4-[2-(4-Benzofuran-3-yl-piperidin-1-yl)-ethyl]-cyclohexyl}-acetamide;
trans-N-{4-[2-(4-Benzofuran-3-yl-piperidin-1-yl)-ethyl]-cyclohexyl}-3-methoxy-propionamide;
Tetrahydro-pyran-4-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-(tetrahydro-pyran-4-yl)-acetamide;
trans-N-{4-[2-(4-Benzofuran-3-yl-piperidin-1-yl)-ethyl]-cyclohexyl}-propionamide;

trans-N-{4-[2-(4-Benzofuran-3-yl-piperidin-1-yl)-ethyl]-cyclohexyl}-2-methoxy-acetamide;
trans-N-{4-[2-(4-Benzofuran-3-yl-piperidin-1-yl)-ethyl]-cyclohexyl}-2-methanesulfonyl-acetamide;
trans-N-{4-[2-(4-Benzofuran-3-yl-piperidin-1-yl)-ethyl]-cyclohexyl}-(RS)-2-[1,4]dioxan-2-yl-acetamide;
trans-N-{4-[2-(4-Benzofuran-3-O-piperidin-1-yl)-ethyl]-cyclohexyl}-benzamide; and
trans-N-{4-[2-(4-Benzofuran-3-yl-piperidin-1-yl)-ethyl]-cyclohexyl}-2-(3-methyl-isoxazol-5-yl)-acetamide;
or a pharmaceutically acceptable salt or ester thereof.

15. The compound of claim 1, selected from the group consisting of:
trans-N-{4-[2-(4-Benzofuran-3-yl-piperidin-1-yl)-ethyl]-cyclohexyl}-2-hydroxy-acetamide;
trans-N-{4-[2-(4-Benzofuran-3-yl-piperidin-1-yl)-ethyl]-cyclohexyl}-3,3,3-trifluoro-propionamide;
trans-N-{4-[2-(4-Benzofuran-3-yl-piperidin-1-yl)-ethyl-]cyclohexyl}-4-morpholin-4-yl-benzamide;
trans-N-{4-[2-(4-Benzofuran-3-yl-piperidin-1-yl)-ethyl]-cyclohexyl}-isobutyramide;
trans-N-{4-[2-(4-Benzofuran-3-yl-piperidin-1-yl)-ethyl]-cyclohexyl}-3-methyl-butyramide;
trans-N-{4-[2-(4-Benzofuran-3-yl-piperidin-1-yl)-ethyl]-cyclohexyl}-2-hydroxy-2-methyl-propionamide;
(RS)-Tetrahydro-furan-3-carboxylic acid trans-{4-[2-(4-benzofuran-3-yl-piperidin-1-yl)-ethyl]-cyclohexyl}-amide;
(RS)-Tetrahydro-furan-2-carboxylic acid trans-{4-[2-(4-benzofuran-3-yl-piperidin-1-yl)-ethyl]-cyclohexyl}-amide;
Quinoline-4-carboxylic acid trans-{4-[2-(4-benzofuran-3-yl-piperidin-1-yl)-ethyl]-cyclohexyl}-amide; and
Cyclobutanecarboxylic acid trans-{4-[2-(4-benzofuran-3-yl-piperidin-1-yl)-ethyl]-cyclohexyl}-amide;
or a pharmaceutically acceptable salt or ester thereof.

16. The compound of claim 1, selected from the group consisting of:
trans-N-{4-[2-(4-Benzofuran-3-yl-piperidin-1-yl)-ethyl]-cyclohexyl}-3-hydroxy-propionamide;
1-Hydroxy-cyclopropanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-cyano-acetamide;
trans-N-{4-[2-(4-Benzofuran-3-yl-piperidin-1-yl)-ethyl]-cyclohexyl}-4-fluoro-benzamide;
trans-N-{4-[2-(4-Benzofuran-3-yl-piperidin-1-yl)-ethyl]-cyclohexyl}-2-cyclopropyl-acetamide;
Tetrahydro-pyran-3-carboxylic acid trans-{4-[2-(4-benzofuran-3-yl-piperidin-1-yl)-ethyl]-cyclohexyl}-amide;
Cyclopropanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2,2-dimethyl-propionamide;
trans-N-{4-[2-(4-Benzofuran-3-yl-piperidin-1-yl)-ethyl]-cyclohexyl}-2-(tetrahydro-furan-2-yl)-acetamide; and
2,2-Difluoro-cyclopropanecarboxylic acid trans-{4-[2-(4-benzofuran-3-yl-piperidin-1-yl)-ethyl]-cyclohexyl}-amide;
or a pharmaceutically acceptable salt or ester thereof.

17. The compound of claim 1, selected from the group consisting of:
trans-N-{4-[2-(4-Benzofuran-3-yl-piperidin-1-yl)-ethyl]-cyclohexyl}-(RS)-2-methyl-butyramide;
trans-N-{4-[2-(4-Benzofuran-3-yl-piperidin-1-yl)-ethyl]-cyclohexyl}-(RS)-3,3,3-trifluoro-2-hydroxy-propionamide;
trans-N-{4-[2-(4-Benzofuran-3-yl-piperidin-1-yl)-ethyl]-cyclohexyl}-butyramide;
trans-N-{4-[2-(4-Benzofuran-3-yl-piperidin-1-yl)-ethyl]-cyclohexyl}-3-hydroxy-3-methyl-butyramide;
trans-N-{-4-[2-(4-Benzofuran-3-yl-piperidin-1-yl)-ethyl]-cyclohexyl}-(R)-4,4,4-trifluoro-3-hydroxy-butyramide;
trans-N-{4-[2-(4-Benzofuran-3-yl-piperidin-1-yl)-ethyl]-cyclohexyl}-methanesulfonamide;
Ethanesulfonic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-methyl-benzenesulfonamide;
trans-N-{4-[2-(4-Benzofuran-3-yl-piperidin-1-yl)-ethyl]-cyclohexyl}-2,2,2-trifluoro-acetamide; and
trans-N-{4-[2-(4-Benzofuran-3-yl-piperidin-1-yl)-ethyl]-cyclohexyl}-3,3-dimethyl-butyramide;
or a pharmaceutically acceptable salt or ester thereof.

18. The compound of claim 1, selected from the group consisting of:
3-Methyl-isoxazole-5-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-N',N'-dimethyl-succinamide;
N'-(trans-4-{2-[4-(benzofuran-3-yl)-piperidin-1-yl]-ethyl}-cyclohexyl)-N,N-dimethylsulfamide;
trans-N-{4-[2-(4-Benzofuran-3-yl-piperidin-1-yl)-ethyl]-cyclohexyl}-4,4,4-trifluoro-butyramide;
4-Methyl-pentanoic acid trans-{4-[2-(4-benzofuran-3-yl-piperidin-1-yl)-ethyl]-cyclohexyl}-amide;
(R)-3-Hydroxy-pentanoic acid trans-{4-[2-(4-benzofuran-3-yl-piperidin-1-yl)-ethyl]-cyclohexyl}-amide;
(S)-3-Hydroxy-pentanoic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-cyclobutyl-acetamide;
trans-N-{4-[2-(4-Benzofuran-3-yl-piperidin-1-yl)-ethyl]-cyclohexyl}-4-chloro-benzamide; and
trans-N-{4-[2-(4-Benzofuran-3-yl-piperidin-1-yl)-ethyl]-cyclohexyl}-4-trifluoromethyl-benzamide;
or a pharmaceutically acceptable salt or ester thereof.

19. The compound of claim 1, selected from the group consisting of:
trans-N-{4-[2-(4-Benzofuran-3-yl-piperidin-1-yl)-ethyl]-cyclohexyl}-4-piperidin-1-yl-benzamide;
trans-N-{4-[2-(4-Benzofuran-3-yl-piperidin-1-yl)-ethyl]-cyclohexyl}-3,3-dimethoxy-propionamide;
3-Methyl-but-2-enoic acid trans-{4-[2-(4-benzofuran-3-yl-piperidin-1-yl)-ethyl]-cyclohexyl}-amide;
(E)-Pent-3-enoic acid trans-{4-[2-(4-benzofuran-3-yl-piperidin-1-yl)-ethyl]-cyclohexyl}-amide;
But-2-ynoic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-formamide;
Pentanoic acid trans-{4-[2-(4-benzofuran-3-yl-piperidin-1-yl)-ethyl]-cyclohexyl}-amide;
Benzo[1,3]dioxole-5-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-pyrazol-1-yl-benzamide; and trans-N-{4-[2-(4-Benzofuran-3-yl-piperidin-1-yl)-ethyl]-cyclohexyl}-4-tert-butyl-benzamide;
or a pharmaceutically acceptable salt or ester thereof.

20. The compound of claim 1, selected from the group consisting of:
trans-N-{4-[2-(4-Benzofuran-3-yl-piperidin-1-yl)-ethyl]-cyclohexyl}-4-(5-methyl-[1,2,4]oxadiazol-3-yl)-benzamide;
trans-N-{4-[2-(4-Benzofuran-3-yl-piperidin-1-yl)-ethyl]-cyclohexyl}-4-(4-methyl-piperazin-1-yl)-benzamide;
Biphenyl-4-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-pyridin-3-yl-benzamide;
trans-N-{4-[2-(4-Benzofuran-3-yl-piperidin-1-yl)-ethyl]-cyclohexyl}-6-morpholin-4-yl-nicotinamide;
trans-N-{4-[2-(4-Benzofuran-3-yl-piperidin-1-yl)-ethyl]-cyclohexyl}-4-(1,1-dioxo-1λ6-thiomorpholin-4-yl)-benzamide;
5-Morpholin-4-yl-pyrazine-2-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-pyrrol-1-yl-benzamide;
trans-N-{4-[2-(4-Benzofuran-3-yl-piperidin-1-yl)-ethyl]-cyclohexyl}-6-methyl-nicotinamide; and
trans-N-{4-[2-(4-Benzofuran-3-yl-piperidin-1-yl)-ethyl]-cyclohexyl}-4-cyano-benzamide;
or a pharmaceutically acceptable salt or ester thereof.

21. The compound of claim 1, selected from the group consisting of:
trans-N-{4-[2-(4-Benzofuran-3-yl-piperidin-1-yl)-ethyl]-cyclohexyl}-4-tert-butoxy-benzamide;
trans-N-{4-[2-(4-Benzofuran-3-yl-piperidin-1-A-ethyl]-cyclohexyl}-2-trans-(4-methoxy-cyclohexyl)-acetamide;
Quinoline-6-carboxylic acid trans-{4-[2-(4-benzofuran-3-yl-piperidin-1-yl)-ethyl]-cyclohexyl}-amide;
trans-2-Benzo[1,3]dioxol-5-yl-N-{4-[2-(4-benzofuran-3-yl-piperidin-1-yl)-ethyl]-cyclohexyl}-acetamide;
5-Methanesulfonyl-thiophene-2-carboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-2-oxetan-3-yl-acetamide;
4-tert-Butyl-cyclohexanecarboxylic acid trans-{4-[2-(4-benzofuran-3-yl-piperidin-1-yl)-ethyl]-cyclohexyl}-amide;
Adamantane-1-carboxylic acid trans-{4-[2-(4-benzofuran-3-yl-piperidin-1-yl)-ethyl]-cyclohexyl}-amide;
4-Trifluoromethyl-cyclohexanecarboxylic acid trans-{4-[2-(4-benzofuran-3-yl-piperidin-1-yl)-ethyl]-cyclohexyl}-amide; and
trans-N-{4-[2-(4-Benzofuran-3-yl-piperidin-1-yl)-ethyl]-cyclohexyl}-4-isobutyl-benzamide;
or a pharmaceutically acceptable salt or ester thereof.

22. The compound of claim 1, selected from the group consisting of:
trans-N-{4-[2-(4-Benzofuran-3-yl-piperidin-1-yl)-ethyl]-cyclohexyl}-4-ethyl-benzamide;
trans-N-{4-[2-(4-Benzofuran-3-yl-piperidin-1-yl)-ethyl]-cyclohexyl}-4-cyclohexyl-benzamide;
trans-N-{4-[2-(4-Benzofuran-3-yl-piperidin-1-yl)-ethyl]-cyclohexyl}-4-isopropyl-benzamide;
trans-N-{4-[2-(4-Benzofuran-3-yl-piperidin-1-yl)-ethyl]-cyclohexyl}-4-cyclopropyl-benzamide;
trans-2-Benzo[d]isoxazol-3-yl-N-{4-[2-(4-benzofuran-3-yl-piperidin-1-yl)-ethyl]-cyclohexyl}-acetamide;
trans-N-{4-[2-(4-Benzofuran-3-yl-piperidin-1-yl)-ethyl]-cyclohexyl}-4-methanesulfonyl-benzamide; and
trans-N-{4-[2-(4-Benzofuran-3-yl-piperidin-1-yl)-ethyl]-cyclohexyl}-2,4-dichloro-benzamide;
trans-N-{4-[2-(4-Benzofuran-3-yl-piperidin-1-yl)-ethyl]-cyclohexyl}-4-tert-butyl-benzenesulfonamide;
or a pharmaceutically acceptable salt or ester thereof.

23. The compound of claim 1, selected from the group consisting of trans-N-{4-[2-(4-Benzofuran-3-yl-piperidin-1-yl-ethyl]-cyclohexyl}-3-methoxy-propionamide;
trans-N-{4-[2-(4-Benzofuran-3-yl-piperidin-1-yl)-ethyl]-cyclohexyl}-2-(tetrahydro-pyran-4-yl)-acetamide;
trans-N-{4-[2-(4-Benzofuran-3-yl-piperidin-1-yl)-ethyl]-cyclohexyl}-2-methoxy-acetamide;
trans-N-{4-[2-(4-Benzofuran-3-yl-piperidin-1-yl)-ethyl]-cyclohexyl}-(RS)-2-[1,4]dioxan-2-yl-acetamide;
trans-N-{4-[2-(4-Benzofuran-3-yl-piperidin-1-yl)-ethyl]-cyclohexyl}-4-morpholin-4-yl-benzamide;
trans-N-{4-[2-(4-Benzofuran-3-yl-piperidin-1-yl)-ethyl]-cyclohexyl}-4-trifluoromethyl-benzamide;
trans-N-{4-[2-(4-Benzofuran-3-yl-piperidin-1-yl)-ethyl]-cyclohexyl}-4-piperidin-1-yl-benzamide;
trans-N-{4-[2-(4-Benzofuran-3-yl-piperidin-1-A-ethyl]-cyclohexyl}-4-tert-butyl-benzamide;
trans-N-{4-[2-(4-Benzofuran-3-yl-piperidin-1-yl)-ethyl]-cyclohexyl}-4-(5-methyl-[1,2,4]oxadiazol-3-yl)-benzamide;
trans-N-{4-[2-(4-Benzofuran-3-yl-piperidin-1-yl)-ethyl]-cyclohexyl}-4-tert-butoxy-benzamide;
4-tert-Butyl-cyclohexanecarboxylic acid trans-{4-[2-(4-benzofuran-3-yl-piperidin-1-yl)-ethyl]-cyclohexyl}-amide;
trans-N-{4-[2-(4-Benzofuran-3-yl-piperidin-1-yl)-ethyl]-cyclohexyl}-4-isobutyl-benzamide;
trans-N-{4-[2-(4-Benzofuran-3-yl-piperidin-1-yl)-ethyl]-cyclohexyl}-4-ethyl-benzamide;
trans-N-{4-[2-(4-Benzofuran-3-yl-piperidin-1-yl)-ethyl]-cyclohexyl}-4-isopropyl-benzamide; and
trans-N-{4-[2-(4-Benzofuran-3-yl-piperidin-1-yl)-ethyl]-cyclohexyl}-4-cyclopropyl-benzamide;
or a pharmaceutically acceptable salt or ester thereof.

24. A pharmaceutical composition comprising a therapeutically effective amount of a compound of formula (I)

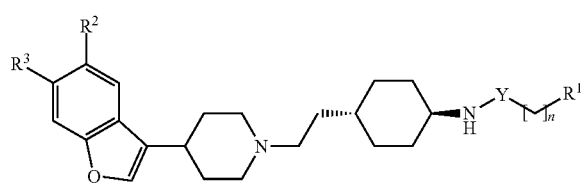

(I)

wherein
n is 0, 1, 2, 3 or 4;
Y is —C(O)— or —S(O)$_2$—;
R$^1$ is hydrogen, alkyl, alkenyl, alkynyl, haloalkyl, cycloalkyl, adamantyl, heterocycloalkyl, aryl, aryl anellated to heterocycloalkyl, heteroaryl, —NR$^6$R$^7$, hydroxy, alkoxy, or haloalkoxy;
wherein alkyl, alkenyl, alkynyl, haloalkyl, alkoxy and haloalkoxy are each optionally substituted by one, two or three independent R$^4$; and wherein cycloalkyl, adamantyl, heterocycloalkyl, aryl, aryl anellated to heterocycloalkyl, and heteroaryl are each optionally substituted by one, two or three independent $R^5$;

$R^2$ and $R^3$ are each independently hydrogen, halogen, cyano, alkyl, haloalkyl, hydroxy, alkoxy or haloalkoxy;

$R^4$ is cyano, cycloalkyl, heterocycloalkyl, aryl, heteroaryl, —C(O)NR$^6$R$^7$, —NR$^6$R$^7$, —NH(CO)-alkyl, hydroxy, alkoxy, haloalkoxy, oxo, or —S(O)$_2$R$^6$;

wherein cycloalkyl, heterocycloalkyl, aryl, and heteroaryl, are each optionally substituted by one, two or three independent $R^5$;

$R^5$ is halogen, cyano, alkyl, haloalkyl, cycloalkyl, heterocycloalkyl, aryl, heteroaryl, —C(O)NR$^6$R$^7$, —NR$^6$R$^7$, —NH(CO)-alkyl, hydroxy, alkoxy, haloalkoxy, oxo, or —S(O)$_2$R$^6$;

wherein cycloalkyl, heterocycloalkyl, aryl, and heteroaryl, are each optionally substituted by one, two or three substituents independently selected from halogen, cyano, alkyl, haloalkyl, hydroxy, alkoxy, haloalkoxy, and oxo;

$R^6$ and $R^7$ are each independently hydrogen, alkyl, haloalkyl, cycloalkyl, cycloalkylalkyl, heterocycloalkyl, heterocycloalkylalkyl, aryl, or heteroaryl;

or a pharmaceutically acceptable salt or ester thereof and a pharmaceutically acceptable carrier.

\* \* \* \* \*